US012416062B2

(12) United States Patent
Watola et al.

(10) Patent No.: US 12,416,062 B2
(45) Date of Patent: Sep. 16, 2025

(54) ENHANCED AUTONOMOUS HANDS-FREE CONTROL IN ELECTRONIC VISUAL AIDS

(71) Applicant: Eyedaptic, Inc., Laguna Niguel, CA (US)

(72) Inventors: David Watola, Irvine, CA (US); Jay E. Cormier, Laguna Niguel, CA (US); Brian Kim, San Clemente, CA (US)

(73) Assignee: Eyedaptic, Inc., Laguna Niguel, CA (US)

( * ) Notice: Subject to any disclaimer, the term of this patent is extended or adjusted under 35 U.S.C. 154(b) by 0 days.

(21) Appl. No.: 18/344,337

(22) Filed: Jun. 29, 2023

(65) Prior Publication Data

US 2024/0126366 A1    Apr. 18, 2024

Related U.S. Application Data

(63) Continuation of application No. 17/278,350, filed as application No. PCT/US2019/052685 on Sep. 24, 2019, now Pat. No. 11,726,561.
(Continued)

(51) Int. Cl.
| C22B 1/00 | (2006.01) |
| A61F 9/08 | (2006.01) |
| C22B 11/00 | (2006.01) |
| C22B 15/00 | (2006.01) |
| G02B 27/01 | (2006.01) |
| G06F 3/01 | (2006.01) |
| G06V 20/10 | (2022.01) |
| G09B 21/00 | (2006.01) |

(52) U.S. Cl.
CPC .................. *C22B 1/00* (2013.01); *A61F 9/08* (2013.01); *C22B 11/00* (2013.01); *C22B 15/00* (2013.01); *G02B 27/0101* (2013.01); *G06F 3/013* (2013.01); *G06V 20/10* (2022.01); *G09B 21/008* (2013.01); *G02B 2027/0138* (2013.01); *G02B 2027/014* (2013.01); *G02B 2027/0178* (2013.01)

(58) Field of Classification Search
None
See application file for complete search history.

(56) References Cited

U.S. PATENT DOCUMENTS

| 5,546,099 A | 8/1996 | Quint et al. |
| 5,777,715 A | 7/1998 | Kruegle et al. |

(Continued)

FOREIGN PATENT DOCUMENTS

| CA | 2916780 A1 | 10/2008 |
| CA | 164180 S | 9/2016 |

(Continued)

OTHER PUBLICATIONS

Carroll et al.; Visual field testing:from one medical student to another; 18 pages; retrieved from the internet (http://eyerounds.org/tutorials/VF-testing/); Aug. 22, 2013.
(Continued)

*Primary Examiner* — Talha M Nawaz
(74) *Attorney, Agent, or Firm* — Shay Glenn LLP

(57) ABSTRACT

Adaptive Control Systems and methods are provided for an electronic visual aid, which may be wearable, hand held or fixed mount, including autonomous hands free control integrated with artificial intelligence tunable to user preferences and environmental conditions.

27 Claims, 9 Drawing Sheets

Related U.S. Application Data

(60) Provisional application No. 62/735,543, filed on Sep. 24, 2018.

(56) References Cited

U.S. PATENT DOCUMENTS

| | | | |
|---|---|---|---|
| 5,892,570 | A | 4/1999 | Stevens |
| 6,418,122 | B1 | 7/2002 | Schoenblum et al. |
| 8,384,999 | B1 | 2/2013 | Crosby |
| 8,976,086 | B2 | 3/2015 | Hilkes |
| 9,516,283 | B2 | 12/2016 | Hilkes et al. |
| 9,782,084 | B2 | 10/2017 | Maertz |
| 10,091,414 | B2 | 10/2018 | Chan et al. |
| 10,347,048 | B2 | 7/2019 | Fu et al. |
| 10,397,560 | B2 | 8/2019 | Miyao et al. |
| 10,429,675 | B2 | 10/2019 | Greget |
| 10,564,714 | B2 | 2/2020 | Marggraff et al. |
| 10,869,026 | B2 | 12/2020 | Gupta |
| 10,872,472 | B2 | 12/2020 | Watola et al. |
| 10,950,049 | B1 | 3/2021 | Kelly et al. |
| 10,963,999 | B2 | 3/2021 | Werblin et al. |
| 10,984,508 | B2 | 4/2021 | Kim et al. |
| 11,016,302 | B2 | 5/2021 | Freeman et al. |
| 11,030,975 | B2 | 6/2021 | Nishibe et al. |
| 11,031,120 | B1 | 6/2021 | Freeman et al. |
| 11,043,036 | B2 | 6/2021 | Kim et al. |
| 11,132,055 | B2 | 9/2021 | Jones et al. |
| 11,187,906 | B2 | 11/2021 | Watola et al. |
| 11,282,284 | B2 | 3/2022 | Watola et al. |
| 11,372,479 | B2 | 6/2022 | Bradley et al. |
| 11,385,468 | B2 | 7/2022 | Watola et al. |
| 11,521,360 | B2 | 12/2022 | Kim et al. |
| 11,546,527 | B2 | 1/2023 | Werblin et al. |
| 11,563,885 | B2 | 1/2023 | Watola et al. |
| 11,676,152 | B2 | 6/2023 | Watola et al. |
| 11,676,352 | B2 | 6/2023 | Watola et al. |
| 11,726,561 | B2 | 8/2023 | Watola et al. |
| 11,756,168 | B2 | 9/2023 | Kim et al. |
| 11,819,273 | B2 | 11/2023 | Freeman et al. |
| 11,956,414 | B2 | 4/2024 | Freeman et al. |
| 12,062,430 | B2 | 8/2024 | Riggs et al. |
| 2007/0200927 | A1 | 8/2007 | Krenik |
| 2008/0013047 | A1 | 1/2008 | Todd et al. |
| 2008/0247620 | A1 | 10/2008 | Lewis et al. |
| 2008/0309878 | A1 | 12/2008 | Hirji |
| 2009/0273758 | A1 | 11/2009 | Wang et al. |
| 2011/0043644 | A1 | 2/2011 | Munger et al. |
| 2011/0109876 | A1 | 5/2011 | Reichow et al. |
| 2011/0181692 | A1 | 7/2011 | Kuno |
| 2011/0227813 | A1 | 9/2011 | Haddick et al. |
| 2011/0285960 | A1 | 11/2011 | Kohn et al. |
| 2012/0206452 | A1 | 8/2012 | Geisner et al. |
| 2012/0244865 | A1 | 9/2012 | Vartanian et al. |
| 2012/0309529 | A1 | 12/2012 | Westlund et al. |
| 2013/0021373 | A1 | 1/2013 | Vaught et al. |
| 2013/0127980 | A1 | 5/2013 | Haddick et al. |
| 2013/0215147 | A1 | 8/2013 | Hilkes et al. |
| 2014/0002475 | A1 | 1/2014 | Oh |
| 2014/0053111 | A1* | 2/2014 | Beckman ............... G06F 3/0481 345/672 |
| 2014/0063062 | A1 | 3/2014 | Fateh |
| 2014/0152530 | A1 | 6/2014 | Venkatesha et al. |
| 2014/0210970 | A1 | 7/2014 | Dalal et al. |
| 2015/0002808 | A1 | 1/2015 | Rizzo, III et al. |
| 2015/0355481 | A1 | 12/2015 | Hilkes et al. |
| 2016/0033771 | A1 | 2/2016 | Tremblay et al. |
| 2016/0037025 | A1 | 2/2016 | Blum |
| 2016/0041615 | A1 | 2/2016 | Ikeda |
| 2016/0085302 | A1 | 3/2016 | Publicover et al. |
| 2016/0116979 | A1 | 4/2016 | Border |
| 2016/0156850 | A1 | 6/2016 | Werblin et al. |
| 2016/0171779 | A1 | 6/2016 | Bar-Zeev et al. |
| 2016/0178912 | A1 | 6/2016 | Kusuda et al. |
| 2016/0180591 | A1 | 6/2016 | Shiu et al. |
| 2016/0187654 | A1 | 6/2016 | Border et al. |
| 2016/0187969 | A1 | 6/2016 | Larsen et al. |
| 2016/0216515 | A1 | 7/2016 | Bouchier et al. |
| 2016/0235291 | A1 | 8/2016 | Goh et al. |
| 2016/0246057 | A1 | 8/2016 | Hasegawa et al. |
| 2016/0264051 | A1 | 9/2016 | Werblin |
| 2016/0270648 | A1 | 9/2016 | Freeman et al. |
| 2016/0270656 | A1 | 9/2016 | Samec et al. |
| 2016/0274381 | A1 | 9/2016 | Haddadi |
| 2016/0314564 | A1 | 10/2016 | Jones et al. |
| 2016/0349509 | A1 | 12/2016 | Lanier et al. |
| 2016/0363770 | A1 | 12/2016 | Kim et al. |
| 2016/0377865 | A1 | 12/2016 | Alexander et al. |
| 2017/0068119 | A1 | 3/2017 | Antaki et al. |
| 2017/0084203 | A1 | 3/2017 | Aguren |
| 2017/0176748 | A1 | 6/2017 | Kim |
| 2017/0185723 | A1 | 6/2017 | McCallum et al. |
| 2017/0200296 | A1 | 7/2017 | Jones et al. |
| 2017/0221264 | A1 | 8/2017 | Perry |
| 2017/0249862 | A1 | 8/2017 | Border |
| 2017/0273552 | A1 | 9/2017 | Leung et al. |
| 2017/0287222 | A1 | 10/2017 | Fujimaki |
| 2017/0343822 | A1 | 11/2017 | Border et al. |
| 2017/0365101 | A1* | 12/2017 | Samec ............... G16H 20/70 |
| 2017/0372225 | A1* | 12/2017 | Foresti ............... G06F 16/285 |
| 2018/0005419 | A1* | 1/2018 | Hao ............... G06F 3/04845 |
| 2018/0052326 | A1 | 2/2018 | Wall et al. |
| 2018/0077409 | A1 | 3/2018 | Heo et al. |
| 2018/0103917 | A1 | 4/2018 | Kim et al. |
| 2018/0104106 | A1 | 4/2018 | Lee et al. |
| 2018/0144554 | A1 | 5/2018 | Watola et al. |
| 2018/0150132 | A1 | 5/2018 | Xiao et al. |
| 2018/0203231 | A1 | 7/2018 | Glik et al. |
| 2018/0217380 | A1 | 8/2018 | Nishimaki et al. |
| 2018/0249151 | A1 | 8/2018 | Freeman et al. |
| 2018/0365877 | A1 | 12/2018 | Watola et al. |
| 2019/0012841 | A1 | 1/2019 | Kim et al. |
| 2019/0041642 | A1 | 2/2019 | Haddick et al. |
| 2019/0204113 | A1 | 7/2019 | He et al. |
| 2019/0279407 | A1 | 9/2019 | McHugh et al. |
| 2019/0331920 | A1 | 10/2019 | Watola et al. |
| 2019/0331922 | A1 | 10/2019 | Kim et al. |
| 2019/0339528 | A1 | 11/2019 | Freeman et al. |
| 2019/0385342 | A1 | 12/2019 | Freeman et al. |
| 2020/0371311 | A1 | 11/2020 | Lobachinsky et al. |
| 2021/0022599 | A1 | 1/2021 | Freeman et al. |
| 2021/0257084 | A1 | 8/2021 | Freeman et al. |
| 2021/0271318 | A1 | 9/2021 | Bradley et al. |
| 2022/0005587 | A1 | 1/2022 | Freeman et al. |
| 2022/0171456 | A1 | 6/2022 | Siddiqi et al. |
| 2023/0044529 | A1 | 2/2023 | Watola et al. |
| 2023/0274507 | A1 | 8/2023 | Kim et al. |
| 2023/0276122 | A1 | 8/2023 | Watola et al. |
| 2024/0061253 | A1 | 2/2024 | Watola et al. |

FOREIGN PATENT DOCUMENTS

| | | |
|---|---|---|
| CA | 3043204 C | 8/2021 |
| CA | 2991644 A1 | 3/2022 |
| CA | 3084546 C | 1/2023 |
| CA | 3069173 C | 5/2023 |
| CN | 104076513 A | 10/2014 |
| CN | 104306102 A | 1/2015 |
| CN | 105930819 A | 9/2016 |
| CN | 112534467 A | 3/2021 |
| CN | 108475001 B | 6/2021 |
| CN | 114063302 A | 2/2022 |
| CN | 110311351 B | 5/2022 |
| CN | 107121070 B | 3/2023 |
| EP | 2674805 A2 | 12/2013 |
| EP | 3830630 A4 | 1/2023 |
| EP | 2621169 B1 | 7/2023 |
| JP | 2017049916 A | 3/2017 |
| JP | 2017120550 A | 7/2017 |
| JP | 2018141874 A | 9/2018 |
| KR | 20140066258 A | 5/2014 |
| WO | WO2008/119187 A1 | 10/2008 |
| WO | WO2011/060525 A1 | 5/2011 |
| WO | WO2013/120180 A1 | 8/2013 |
| WO | WO2013/177654 A1 | 12/2013 |

(56) References Cited

FOREIGN PATENT DOCUMENTS

| WO | WO2014/107261 A1 | 7/2014 |
| WO | WO2016/017081 A1 | 2/2016 |
| WO | WO2016/036860 A1 | 3/2016 |
| WO | WO2016/077343 A1 | 5/2016 |
| WO | WO2016/144419 A1 | 9/2016 |
| WO | WO2016/149536 A1 | 9/2016 |
| WO | WO2016/168913 A1 | 10/2016 |
| WO | WO2017/059522 A1 | 4/2017 |
| WO | WO2018/200717 A1 | 11/2018 |
| WO | WO2020/014705 A1 | 1/2020 |
| WO | WO2020/014707 A1 | 1/2020 |
| WO | WO2021/003406 A1 | 1/2021 |

OTHER PUBLICATIONS

Gonzalez; Advanced Imaging in Head-Mounted Displays for Patients with Age-Related Macular Degeneration; Doctoral dissertation; Technical University of Munich; p. 1-129; 2011 (the year of publication is sufficiently earlier than the effective U.S. filing date and any foreign priority date so that the particular month of publication is not in issue).

Hwang et al.; An augmented-reality edge enhancement application for Google Glass; Optometry and vision science; 91(8); pp. 1021-1030; Aug. 1, 2014.

Nomoto et al.; Prototype and evaluation of magnifying reader using image processing; Proceedings of the 2011 JSME Conference on Robotics and Mechatronics; The Japan Society of Mechanical Engineers; pp. 2784-2785; (Abstract Only) May 2011.

Unser et al.; B-spline signal processing: Part II—efficient design and applicationtions; IEEE Transactions on Signal Processing; 41(2); pp. 834-848; Feb. 1993.

Unser et al.; B-spline signal processing: part I—theory; IEEE Transactions on Signal Processing: 41(2)); pp. 821-832; Feb. 1993.

Unser et al.; TheL2 polynomial spline pyramid; IEEE Transactions on Pattern Analysis and Machine Intelligence; 15(4); pp. 364-379; Apr. 1993.

Unser; Splines—a perfect fit for signal and image processing; IEEE Signal Processing Magazine; 16 (Article); pp. 22-38; Nov. 1999.

Watola et al.; U.S. Appl. No. 18/310,095 entitled "Systems for augmented reality visual aids and tools," filed May 1, 2023.

Watola et al.; U.S. Appl. No. 18/675,974 entitled "Systems for augmented reality visual aids and tools," filed May 28, 2024.

Watola et al.; U.S. Appl. No. 18/898,388 entitled "Adaptive system for autonomous machine learning and control in wearable augmented reality and virtual reality visual aids," filed Sep. 26, 2024.

\* cited by examiner

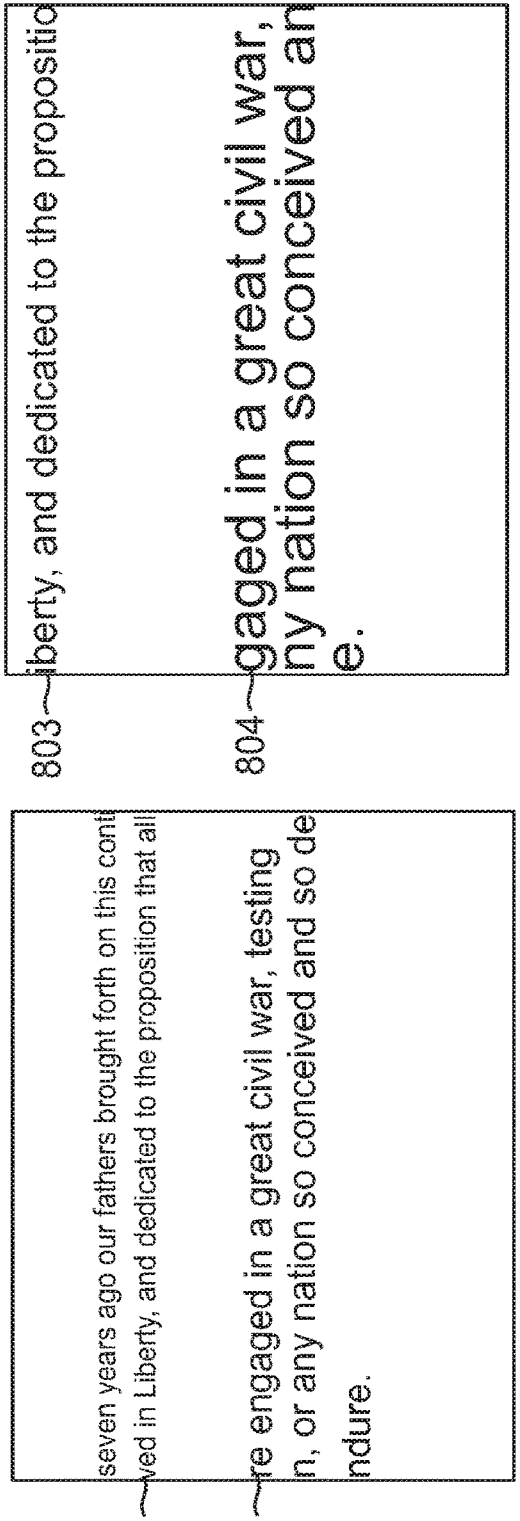
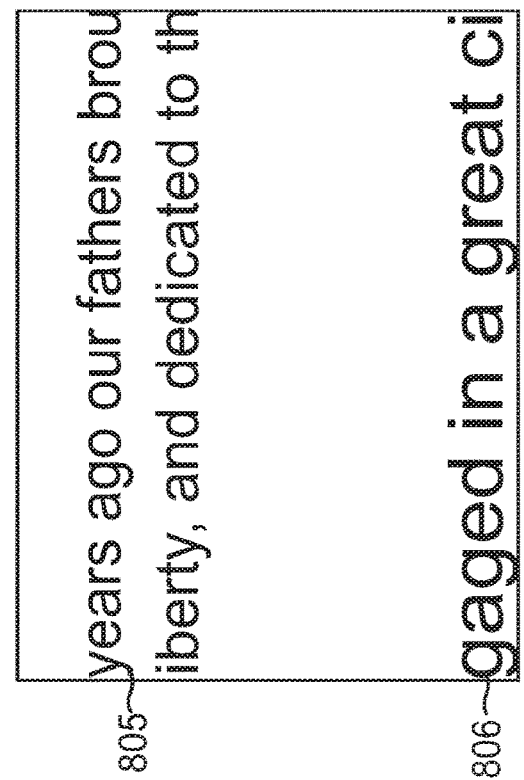
FIG. 4A
FIG. 4B
FIG. 4C

FIG. 5D

ENHANCED AUTONOMOUS HANDS-FREE CONTROL IN ELECTRONIC VISUAL AIDS

CROSS REFERENCE TO RELATED APPLICATIONS

This patent application is a continuation of U.S. Patent Application Ser. No. 17/278,350, filed Mar. 22, 2021, which is a national phase application under 35 USC 371 of International Patent No. PCT/US2019/052685, filed Sep. 24, 2019, titled "Enhanced Autonomous Hands-Free Control in Electronic Visual Aids", which claims priority to U.S. Provisional Patent Application No. 62/735,643, filed Sep. 24, 2018, titled "Novel Enhanced Autonomous Hands-free Control in Electronic Visual Aids," which is herein incorporated by reference in its entirety.

This application is related to PCT Pat. App. No. PCT/US2017/062421, filed Nov. 17, 2017, U.S. Ser. No. 15/817,117, filed Nov. 17, 2017, U.S. Ser. No. 15/918,884, filed Mar. 12, 2018, U.S. Ser. No. 16/030,788, filed Jul. 9, 2018, U.S. Ser. No. 16,177,333, filed Oct. 31, 2018, U.S. Ser. No. 16/294,601, filed Mar. 6, 2019, and PCT Pat. App. No. PCT/US2019/034443, filed May 29, 2019, the contents of which are incorporated herein by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Visual aids have been used for hundreds of years, and as in the past are commonly optics-based solutions such as eyeglasses. The conceptualization and early experimentation with programmable head mounted electronic based visual aids began with NASA-funded research in the late 1980s. Basic functionality described included remapping of pixels in order to manipulate the image presented to the wearer's eye. At the same time personal computer and mobile technology was becoming mainstream and widely programmable for a variety of other tasks, including low vision applications.

Current hardware implementations of electronic visual aids include many forms such as e-readers, computer plug-ins with low vision accessibility features, mobile devices such as cellular smart phones, dedicated electronic magnifiers, Virtual Reality (VR) headsets, and Augmented Reality (AR) glasses. These platforms are designed and intended for use in a number of applications such as gaming, telepresence, and a wide variety of enterprise applications.

SUMMARY

Examples described herein generally relate to improved hardware and integrated software and algorithms for a wide range of electronic visual aids, including personal computer and mobile technology, electronic e-readers, and wearable electronic Augmented Reality (AR) and Virtual Reality (VR) glasses in general, with additional specific benefits for low-vision users suffering from various visual impairments (e.g., Age-related Macular Degeneration— AMD— and other visual field deficiencies). The electronic visual aids described herein resolve a problem previously addressed by brute-force methods that ultimately reduce the usability and versatility of existing visual aids. The updated approaches described herein further enhance the experience of low-vision users without sacrificing key benefits of the standard design. This includes autonomous control features that take into account usage habits and environmental patterns. In certain applications, normally-sighted users will also benefit from these changes.

Embodiments described herein relate to the automatic setting and adjustment of controls for a wearable, hand-held, or mounted personal electronic visual aid, which can assist users suffering from various visual impairments (e.g., Age-related Macular Degeneration—AMD— and other visual field deficiencies) by improving their ability to perceive and interpret their surroundings. It can also help normally-sighted users locate and view difficult-to-see objects. Such devices incorporate one or more cameras (i.e., image sensors and supporting optics) to capture a continuous stream of environmental images, some form of low-latency processing to combine, adjust, augment, or enhance the images in ways that suit the needs of the user, and one or more displays to present the modified images for real-time viewing.

An effective visual aid must perform sophisticated image processing operations that consider not only the user's visual ability or disease state (if any), but also the user's personal preferences, the current environment, and the desired focus of attention. Although the particulars of disease state and preferences can be effectively captured as stored device settings, manual optimization of initial user-dependent technical configuration parameters is a painstaking process that generally lies beyond the capabilities of untrained personnel; for the vision impaired or technophobic, it is completely unfeasible without assistance. Similarly, the timely manipulation of detailed controls in response to transient circumstances can also be challenging, particularly for elderly users with reduced manual dexterity. Even able-bodied users would prefer to avoid the distraction of fumbling for controls to make an adjustment instead of concentrating on the viewing task.

One way to address these concerns is by incorporating a degree of autonomy into the visual aid, allowing it to infer the user's immediate needs or intentions and act preemptively on his or her behalf. Decisions would ideally be predicated on an assessment of the situation via analysis of image contents, ancillary sensor data, and historical user actions under similar circumstances.

Visual aid systems and methods are provided herein with reliable autonomy and hands-free operation. The systems and methods described herein are configured to identify regions within an input image that contain organized or hierarchical patterns of smaller fundamental structures (e.g., words, lines, or paragraphs comprising individual letters or histograms, rows of glyph-like shapes, or columns of pictograms) and adjust the viewing device (or facilitates such adjustment) so that the meaningful content is more readily discerned or recognized. The systems and methods described herein not only exert control over the degree of magnification provided, but also manipulate the size and nature of the field-of-view. It can also influence the focus of attention by actively drawing notice to autonomously-selected features. These processes are guided by additional non-video information about the goals and intentions of the wearer as inferred from measurements of head and/or eye motion. Subsequently, adjustments to the view can be constrained to times when the changes will be helpful rather than distracting or disorienting.

The systems and methods presented herein are suitable for continuous real-time operation on standalone portable devices possessing limited battery capacity and tightly-constrained computing resources. Although the most economical implementations are strictly user-independent, the design readily scales to more capable platforms by incorporating Machine Learning techniques for more complex recognitions or higher-quality decisions attuned to specific users.

Also presented are complementary systems and methods that autonomously enhance or adjust the contrast of displayed images. This technique shares the same advantages of low complexity for economical real-time implementation when separately implemented, and further benefits from shared components when coupled to the autonomous system that controls magnification and/or field-of-view characteristics.

An electronic visual aid device is provided, comprising a frame configured to be handheld, stationary, or worn on the head of a user, at least one display disposed on or within the frame and configured to display video images, a processor disposed on or in the frame and configured to process the video to produce an enhanced video stream that is displayed on the at least one display. In some embodiments, the electronic visual aid device can include a camera disposed on or in the frame and configured to generate unprocessed real-time video images. In this example, the at least one display can be configured to display the real-time video images, and the processor can be configured to produce the enhanced video stream from the real-time video images.

In one example, the device further comprises an input device configured to receive an input from the user regarding a type and/or an amount of enhancement to apply to the unprocessed real-time video images. In some examples, the input device comprises a physical mechanism. In other examples, the input device comprises a microphone disposed on or in the housing configured to receive voice commands from the user.

In some examples the device includes one or more inertial measurement units to capture the motion of the device and user. These sensors are further used to sense and gather motion in order to establish, develop and refine usage patterns for improved autonomous control.

A method of providing enhanced vision for a low-vision user is also provided, comprising generating and/or receiving unprocessed real-time video images with a camera, processing the unprocessed real-time video images to produce an enhanced video stream, and displaying the enhanced video stream on a display to enter the first eye of the user.

In other examples, the method further comprises processing the unprocessed real-time video images such that the video stream is enhanced when compared to the unprocessed real-time video images. In one example, the enhanced video stream is at least partially magnified when compared to the unprocessed real-time video images. In another example, the enhanced video stream is magnified in a central portion of the video stream. In one example, a portion of the video stream outside of the central portion is magnified less than the central portion but more than the unprocessed real-time video images.

A method of providing autonomous enhancements to a video output of a visual aid device is provided, comprising obtaining real-time images of a scene with the visual aid device, evaluating a motion component of the visual aid device, determining a motion state of the visual aid device based on the motion component, if the motion state indicates that a user of the visual aid device is engaged in an animated movement state, presenting first video images on a display of the visual aid device without additional enhancements or adjustments applied to the real-time images, if the motion state indicates that the user of the visual aid device is engaged in a focused attention state, identifying a subset of the real-time images corresponding to a focus-of-attention of a user of the visual aid device, locating structures of interest from the subset of the real-time images, applying visual enhancements to at least the structures of interest, and presenting second video images including the visually enhanced structures of interest on the display of the visual aid device.

In some embodiments, the motion component comprises an angular velocity of the visual aid device. In another example, the motion component comprises an angular velocity on a yaw axis and a pitch axis of the visual aid device. Additionally, the motion component can comprise translational motion of the visual aid device.

In one embodiment, the animated movement state indicates that the user of the visual aid device is engaged in animated movement, and is therefore not engaged in deliberate concentration or attempting to focus on something within a field of view of the user.

In another embodiment, the focused attention state indicates that the user of the visual aid device is deliberately concentrating on something within the field of view.

In some embodiments, a high angular velocity indicates a sudden change of the focus-of-attention of the user. In other embodiments, small angular velocities of the visual aid device are used to determine that the motion state comprises the focused attention state. In some embodiments, intermediate angular velocities of the visual aid device are used to determine that the motion state comprises the focused attention state. Furthermore, angular velocities associated with reading, scanning, or searching behavior are used to determine that the motion state comprises the focused attention state.

In some examples, the first video images comprise a nominal, unenhanced view with minimal processing and/or magnification.

In one embodiment, the structures of interest comprise text-like structures. Additionally, the structures of interest can comprise facial features. In further embodiments, the structures of interest are selected from the group consisting of letters, numerals, pictograms, glyphs and icons.

In some examples, the visual enhancements comprise adjusting a magnification of at least the structures of interest. In other examples, the visual enhancements comprise adjusting a contrast component of at least the structures of interest.

In one embodiment, determining a motion state of the visual aid device comprises evaluating the motion component associated with a few recent frames of the real-time images to categorize short-term movement of the user of the visual aid device, and evaluating the motion component of more than a few recent frames of the real-time images to identify a specific action state of the user of the visual aid device.

In some embodiments, the method further comprises applying a machine learning algorithm to identify the specific action state.

A method of providing enhanced vision for a low-vision user is also provided, comprising the steps of receiving real-time video images with a visual aid device, identifying, with the visual aid device, a subset of each of the real-time video images corresponding to a focus of attention of the low-vision user, extracting, with the visual aid device, structures of interest within the subset of each of the real-time video images, identifying, with the visual aid device, at least one group of structures of interest that are organized in a row or column, determining, with the visual aid device, a dimension of the at least one group of structures of interest, adjusting, with the visual aid device, a magnification of the at least one group of structures of interest to match a preferred structure dimension, forming, with the visual aid device, an enhanced video stream that includes the real-time images and the at least one group of structures of interest with adjusted magnification, and displaying the enhanced video stream on a display of the visual aid device.

In some embodiments, the subset comprises a fixed area of pixels within each of the real-time video images. In another embodiment, the fixed area of pixels is at a central portion of each of the real-time video images.

In one embodiment, the structures of interest comprise text-like structures. Additionally, the structures of interest can comprise facial features. In further embodiments, the structures of interest are selected from the group consisting of letters, numerals, pictograms, glyphs and icons.

In one embodiment, the visual aid device automatically identifies the subset of each of the real-time video images based on behavioral trends of a user of the visual aid device. In some examples, the behavioral trends of the user comprise a user history of input control sequences and a timing of these input control sequences. In some embodiments, the visual aid device automatically identifies the subset of each of the real-time video images based on the contents of previously processed video images.

In one embodiment, the method further comprises tracking a gaze of the low-vision user with the visual aid device, and wherein the visual aid device automatically identifies the subset of each of the real-time video images based on the gaze of the low-vision user.

In some examples, the method further comprises preprocessing the subset of real-time video images to reduce noise or accommodate other unwanted interference patterns. In one example, the preprocessing comprises enhancing a contrast component of the subset of real-time video images. In another example, the preprocessing comprises increasing a sharpness component of the subset of real-time video images. In yet another example, the preprocessing comprises increasing a detail component of the subset of real-time video images.

In some embodiments, the extracting step further comprises extracting maximally stable extremal regions from the subset of real-time video images.

In one embodiment, the method further comprises examining the extracted structures of interest with the visual aid device, and discarding structures of interest that include parameters that are outside of pre-selected bounds. In some embodiments, the pre-selected bounds may include a length threshold parameter, a width threshold parameter, a pixel-count threshold parameter, or an aspect ratio threshold parameter.

In some embodiments, the method further includes discarding structures of interest that intersect a boundary of the focus of attention of the low-vision user. In another embodiment, the method comprises discarding structures of interest that intersect a top or bottom boundary of the focus of attention of the low-vision user.

In one embodiment, identifying the at least one group of structures of interest that are organized in a row or column further comprises modeling a probability density function of vertical centers for the structures of interest, wherein the probability density function includes one or more pdf peaks, identifying a maximum peak from the pdf peaks of the probability density functions, and retaining only structures of interest that are statistically likely to be associated with the maximum peak. Structures of interest that are statistically likely to be associated with the maximum peak may comprise structures of interest that are consistent in size.

In one embodiment, the method can further comprise determining, with the visual aid device, a statistical confidence that the at least one group of structures of interest are organized in a row or column.

In some examples, adjusting a magnification of at least one group of structures of interest further comprises adjusting a magnification of the at least one group of structures of interest to match the preferred structure size when the statistical confidence is above a confidence threshold.

In another embodiment, the receiving step further comprises obtaining real-time video images with a camera of the visual aid device, and receiving the real-time video images from the camera with a visual aid device.

In some examples, the method further comprises sensing a motion component of the visual aid device as it obtains the real-time video images, determining a motion state of the visual aid device based on the sensed motion component, and wherein the adjusting a magnification step, the forming an enhanced video stream step, and the displaying the enhanced video stream step are performed only if the motion state comprises a focused attention state.

In one example, the method further comprises sensing the motion component of the camera with a gyroscope of the visual aid device, or sensing the motion component of the camera with an accelerometer of the visual aid device.

In another embodiment, the method further comprises displaying the enhanced video stream on a second display. In this example, the display is positioned in front of a first eye of the user and the second display is positioned in front of a second eye of the user.

A method of providing autonomous enhancements to a video output of a visual aid device is also provided, comprising obtaining real-time images of a scene with the visual aid device, updating a maintained motion model of the visual aid device, if the maintained motion model indicates that the user of the visual aid device is engaged in a focused attention state, identifying a subset of the real-time images corresponding to a focus-of-attention of a user of the visual aid device, analyzing only the subset of the real-time images, determining if autonomous visual enhancements are to be applied to the subset of real-time images.

In one embodiment, if autonomous visual enhancements are to be applied to the subset of real-time images, the method further comprises forming an enhanced video stream with autonomous visual enhancements applied to at least the subset of real-time images, and displaying the enhanced video stream to the user.

In some examples, the autonomous visual enhancements comprise adjusting a magnification of at least the subset of real-time images. In other embodiments, the autonomous visual enhancements comprise adjusting a contrast component of the subset of real-time images.

In one embodiment, updating the motion model further comprises evaluating a motion component associated with a few recent frames of the real-time images to categorize a short-term movement of a user of the visual aid device, evaluating the motion component of more than a few recent frames of the real-time images to identify a specific action state of the user of the visual aid device.

In some embodiments, the motion component comprises an angular velocity of the visual aid device, comprises an angular velocity on a yaw axis and a pitch axis of the visual aid device, comprises translational motion of the visual aid device, or comprises an amount of eye movement measured with an eye tracking element of the visual aid device In one embodiment, a high angular velocity is used by the motion model to indicate a sudden change of the focus-of-attention of the user. In another embodiment, a small angular velocity of the visual aid device is used by the motion model to indicate the user is in the focused attention state. In yet another embodiment, an intermediate angular velocity of the visual aid device is used by the motion model to indicate the user is in the focused attention state.

In some embodiments, angular velocities associated with reading, scanning, or searching behavior are used by the motion model to indicate the user is in the focused attention state.

In one example, updating the motion model further comprises identifying a specific action state of the user of the visual aid device based on predicted motions. In another embodiment, updating the motion model further comprises identifying a specific action state of the user of the visual aid device based on historical motions in similar situations.

In some examples, the method further comprises, if the motion state indicates that a user of the visual aid device is engaged in an animated movement state, applying no additional analysis or processing to the real-time images.

In one embodiment, the focused attention state indicates that the user of the visual aid device is deliberately concentrating on something within the field of view.

In another embodiment, the method further comprises identifying user inputs requesting that manual visual enhancements be applied to the real-time images, determining if the manual visual enhancements override the autonomous visual enhancements, and applying the appropriate manual visual enhancements or autonomous visual enhancements to the real-time video images.

A visual aid device is provided, comprising a camera configured to generate real-time video images, a sensor configured to measure at least one motion component of the visual aid device, a display, and a processor configured to determine a motion state of the visual aid device based on the at least one motion component, wherein if the motion state indicates that a user of the visual aid device is engaged in an animated movement state, the processor is further configured to present first video images on the display without additional enhancements or adjustments applied to the real-time images, and wherein if the motion state indicates that the user of the visual aid device is engaged in a focused attention state, the processor is further configured to identify a subset of the real-time images corresponding to a focus-of-attention of a user of the visual aid device, the processor is configured to locate structures of interest from the subset of the real-time images, the processor is configured to apply visual enhancements to at least the structures of interest, and the processor is configured to present second video images including the visually enhanced structures of interest on the display.

In some embodiments, the sensor comprises at least one accelerometer or at least one gyroscope.

In one embodiment, the motion component comprises an angular velocity of the visual aid device, an angular velocity on a yaw axis and a pitch axis of the visual aid device, or translational motion of the visual aid device.

In some embodiments, the animated movement state indicates that the user of the visual aid device is engaged in animated movement, and is therefore not engaged in deliberate concentration or attempting to focus on something within a field of view of the user.

In another embodiment, the focused attention state indicates that the user of the visual aid device is deliberately concentrating on something within the field of view.

In some embodiments, the processor uses small angular velocities of the visual aid device to determine that the motion state comprises the focused attention state. In some embodiments, the processor uses intermediate angular velocities of the visual aid device to determine that the motion state comprises the focused attention state. In further embodiments, the processor uses angular velocities associated with reading, scanning, or searching behavior to determine that the motion state comprises the focused attention state.

In one embodiment, the first video images comprise a nominal, unenhanced view with minimal processing and/or magnification.

In some embodiments, the structures of interest comprise text-like structures or facial features. In additional embodiments, the structures of interest are selected from the group consisting of letters, numerals, pictograms, glyphs and icons.

In some embodiments, the visual enhancements comprise an adjusted magnification of at least the structures of interest, or an adjusted contrast component of at least the structures of interest.

A non-transitory computing device readable medium having instructions stored thereon that are executable by a processor to cause a computing device to obtain real-time images of a scene with the visual aid device, evaluate a motion component of the visual aid device, determine a motion state of the visual aid device based on the motion component, wherein if the motion state indicates that a user of the visual aid device is engaged in an animated movement state, the instructions are executable by the processor to cause the computing device to present first video images on a display of the visual aid device without additional enhancements or adjustments applied to the real-time images, and wherein if the motion state indicates that the user of the visual aid device is engaged in a focused attention state, the instructions are executable by the processor to cause the computing device to identify a subset of the real-time images corresponding to a focus-of-attention of a user of the visual aid device, locate structures of interest from the subset of the real-time images, apply visual enhancements to at least the structures of interest, and present second video images including the visually enhanced structures of interest on the display of the visual aid device.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 4A is an example of an unprocessed camera image of a scene containing only text, taken directly from its source camera and shown to the user on a display.

FIG. 4B is a correspondingly magnified version of the FIG. 4A.

FIG. 4C is a further magnified version of FIG. 4A with a different FOA (Focus of Attention).

FIG. 5A illustrates sample detected shapes in an image of dark text on a light background.

FIG. 5B demonstrates how the detected shapes in FIG. 5A facilitate the selection of simple one-dimensional linear regions having relatively few pixels while containing sufficient information to compute contrast control signals for enhanced viewing of the detected objects.

FIG. 5C demonstrates how the detected shapes in FIG. 5A facilitate the selection of simple two-dimensional areas of pixels to be analyzed that give improved results over the smaller linear regions in FIG. 5B without greatly increasing complexity.

FIG. 5D demonstrates how the detected shapes in FIG. 5A facilitate the selection of a comprehensive but minimal two-dimensional area of pixels to be analyzed for computing contrast control signals.

Figure 1A:
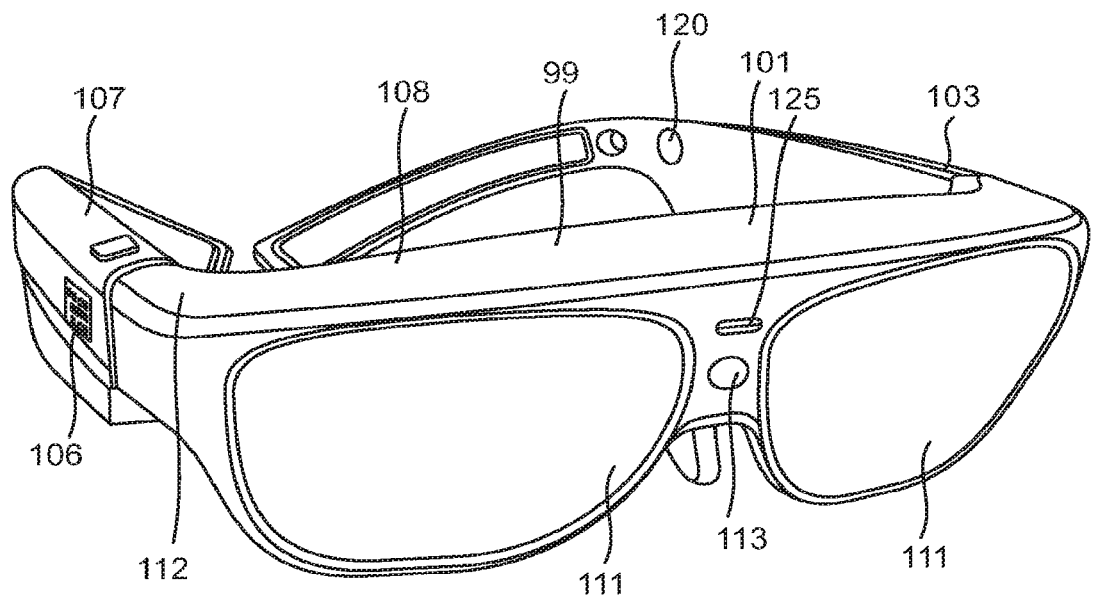
FIG. 1A is one example of an electronic visual aid device according to the present disclosure.
Figure 1B:
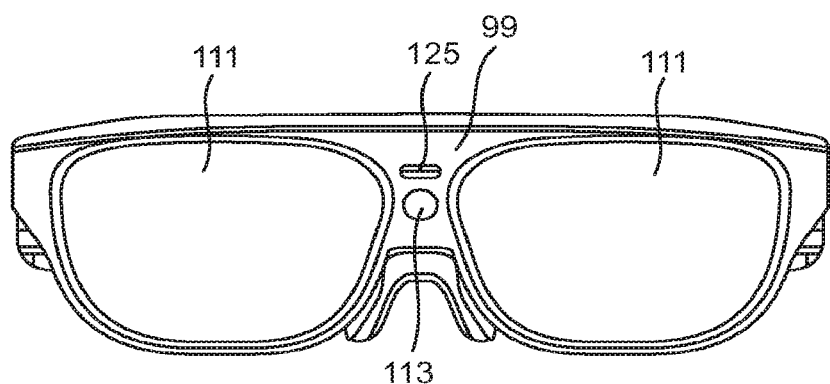
FIG. 1B is one example of an electronic visual aid device according to the present disclosure.
Figure 1C:
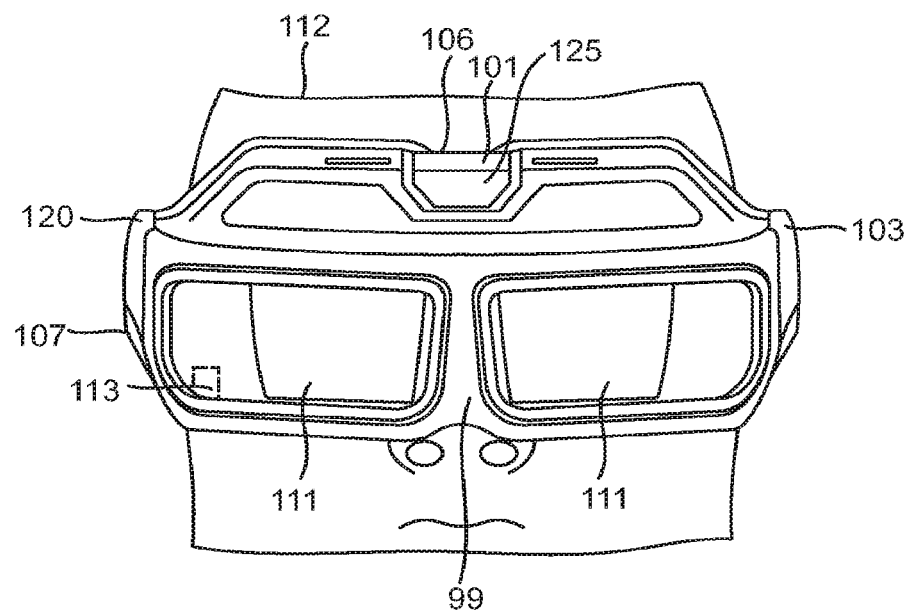
FIG. 1C is one example of an electronic visual aid device according to the present disclosure.
Figure 1D:
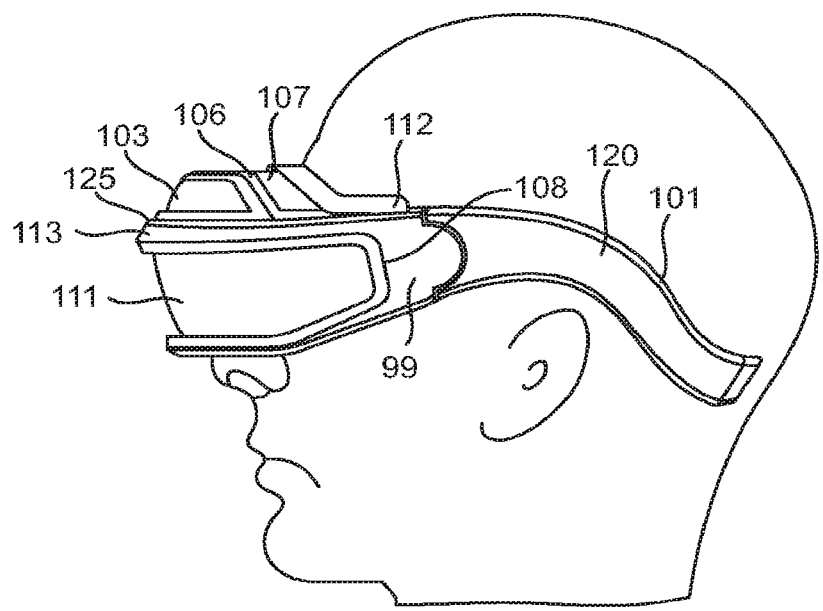
FIG. 1D is one example of an electronic visual aid device according to the present disclosure.

Various preferred embodiments are described herein with references to the drawings in which merely illustrative views are offered for consideration, whereby:

Corresponding reference characters indicate corresponding components throughout the several views of the drawings. Skilled artisans will appreciate that elements in the figures are illustrated for simplicity and clarity, and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

DETAILED DESCRIPTION

The present disclosure is related to systems, methods, computing device readable media, and devices for providing enhanced vision to persons, users, or patients with low vision, particularly low vision in a center of the user's field of view (FOV).

For people with retinal diseases, adapting to loss of vision becomes a way of life. This impacts their lives in many ways including loss of the ability to read, loss of income, loss of mobility and an overall degraded quality of life. By way of example, these disease states may take the form of age-related macular degeneration, retinitis pigmentosa, diabetic retinopathy, Stargardt's disease, and other diseases where damage to part of the retina impairs vision. With prevalent retinal diseases such as AMD (Age-related Macular Degeneration) not all of the vision is lost, and in this case the peripheral vision remains intact as only the central vision is impacted by the degradation of the macula. Given that the peripheral vision remains intact it is possible to take advantage of eccentric viewing by enhancing and optimizing the peripheral vision while perceptually maintaining the FOV which otherwise decreases with increased magnification. The present disclosure described herein supplies novel systems and methods to enhance vision, and also provides simple but powerful hardware enhancements that work in conjunction with advanced software to provide a more natural field of view in conjunction with augmented images.

Electronic visual aid devices as described herein can be constructed from a non-invasive, wearable electronics-based AR eyeglass system (see FIGS. 1A-1E) employing any of a variety of integrated display technologies, including LCD, OLED, or direct retinal projection. Materials are also able to be substituted for the "glass" having electronic elements embedded within the same, so that "glasses" may be understood to encompass for example, sheets of lens and camera containing materials, IOLs, contact lenses and the like functional units. These displays are placed in front of the eyes so as to readily display or project a modified or augmented image when observed with the eyes. This is commonly implemented as a display for each eye, but may also work for only one display as well as a continuous large display viewable by both eyes.

Referring now to FIGS. 1A-1D, wearable electronic visual aid device 99 is housed in a glasses frame model including both features and zones of placement which are interchangeable for processor 101, charging and dataport 103, dual display 111, control buttons 106, accelerometer gyroscope magnetometer 112, Bluetooth/Wi-Fi 108, autofocus camera 113, flashlight 125, and speaker/microphone combinations 120, known to those skilled in the art. For example, batteries 107, including lithium-ion batteries shown in a figure, or any known or developed other versions, functioning as a battery. Power management circuitry is contained within or interfaces with or monitors the battery to manage power consumption, control battery charging, and provide supply voltages to the various devices which may require different power requirements.

As shown in FIG. 1A-1E, any basic hardware can be constructed from a non-invasive, wearable electronics-based AR eyeglass system (see FIGS. 1A-1E) employing any of a variety of integrated display technologies, including LCD, OLED, or direct retinal projection. Materials are also able to be substituted for the "glass" having electronic elements embedded within the same, so that "glasses" may be understood to encompass for example, sheets of lens and camera containing materials, IOLs, contact lenses and the like functional units.

One or more cameras (still, video, or both) 113, mounted on or within the glasses, are configured to continuously monitor the view where the glasses are pointing and continuously capture images that are stored, manipulated and used interactively in the wearable electronic visual aid device. In addition, one or more of these cameras may be IR (infrared) cameras for observation and monitoring in a variety of lighting conditions. The electronic visual aid device can also contain an integrated processor or controller and memory storage (either embedded in the glasses, or tethered by a cable) with embedded software implementing real-time algorithms configured to modify the images as they are captured by the camera(s). These modified, or corrected, images are then continuously presented to the eyes of the user via the displays.

The processes described herein are implemented in an electronic visual aid device configured to present an image or a real-time stream of video to the user. The processes may be implemented in computer programs (also known as programs, software, software applications or code) include machine instructions for a programmable processor, and can be implemented in a high-level procedural and/or object-oriented programming language, and/or in assembly/machine language, such as machine readable code or machine executable code that is stored on a memory and executed by a processor. Input signals or data is received by the unit from a user, cameras, detectors or any other device. Other kinds of devices can be used to provide for interaction with a user as well; for example, feedback provided to the user can be any form of sensory feedback (e.g., visual feedback, auditory feedback, or tactile feedback; and input from the user can be received in any form, including acoustic, speech, or tactile input. Output is presented to the user in any manner, including a screen display or headset display. The processor and memory can be integral components of the electronic visual aid device shown in FIGS. 1A-1D, or can be separate components linked to the electronic visual aid device. Other devices such as mobile platforms with displays (cellular phones, tablets etc.) electronic magnifiers, and electronically enabled contact lens are also able to be used.

Figure 1E:
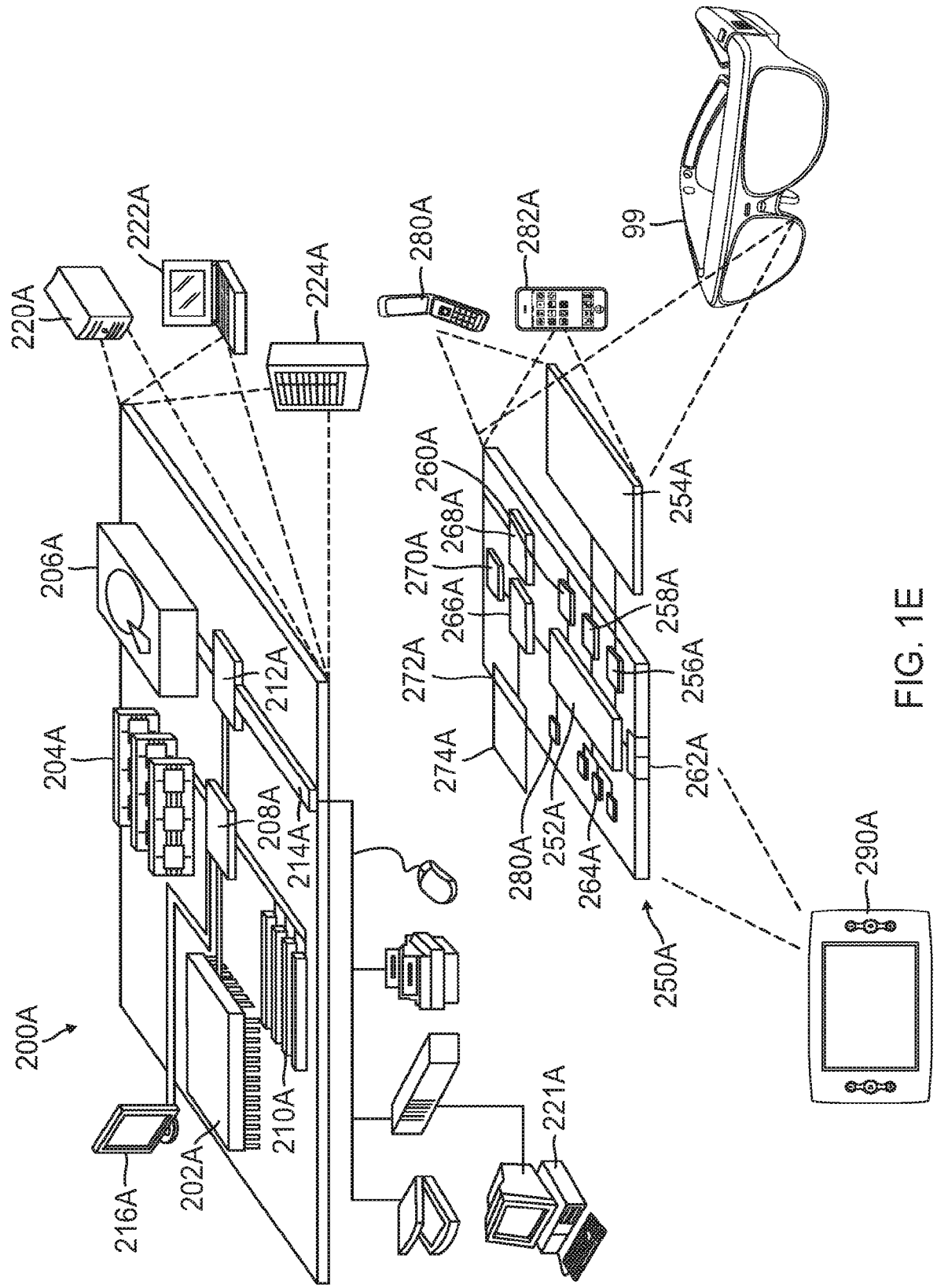
FIG. 1E is one example of an electronic visual aid device, including some of the detailed components, according to the present disclosure.

FIG. 1E is a block diagram showing example or representative computing devices and associated elements that may be used to implement the methods and serve as the apparatus described herein. FIG. 1E shows an example of a generic computing device 200A and a generic mobile computing device 250A, which may be used with the techniques described here. Computing device 200A is intended to represent various forms of digital computers, such as laptops, desktops, workstations, personal digital assistants, servers, blade servers, mainframes, and other appropriate computers. Computing device 250A is intended to represent various forms of mobile devices, such as personal digital assistants, cellular telephones, smart phones, and other similar computing devices that can act and are specifically made for electronic visual aids. The components shown here, their connections and relationships, and their functions, are meant to be exemplary only, and are not meant to limit implementations of the inventions described and/or claimed in this document.

The systems and techniques described here can be implemented in a computing system (e.g., computing device 200A and/or 250A) that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network) ("WAN") and the Internet.

The computing system can include clients and servers. A client and server are generally remote from each other and typically interact through a communication network. The relationship of client and server arises by virtue of computer programs running on the respective computers and having a client-server relationship to each other.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback; and input from the user can be received in any form, including acoustic, speech, or tactile input.

In an example embodiment, computing devices 200A and 250A are configured to receive and/or retrieve electronic documents from various other computing devices connected to computing devices 200A and 250A through a communication network, and store these electronic documents within at least one of memory 204A, storage device 206A, and memory 264A. Computing devices 200A and 250A are further configured to manage and organize these electronic documents within at least one of memory 204A, storage device 206A, and memory 264A using the techniques described here, all of which may be conjoined with, embedded in or otherwise communicating with electronic visual aid device 99.

The memory 204A stores information within the computing device 200A. In one implementation, the memory 204A is a volatile memory unit or units. In another implementation, the memory 204A is non-volatile memory unit or units. In another implementation, the memory 204A is a non-volatile memory unit or units. The memory 204A may also be another form of computer-readable medium, such as a magnetic or optical disk.

The storage device 206A is capable of providing mass storage for the computing device 200A. In one implementation, the storage device 206A may be or contain a computer-200A. In one implementation, the storage device 206A may be or contain a computer-reading medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 204A, the storage device 206A, or memory on processor 202A.

The high speed controller 208A manages bandwidth-intensive operations for the computing device 200A, while the low-speed controller 212A manages lower bandwidth-intensive operations. Such allocation of functions is exemplary only. In one implementation, the high-speed controller 208A is coupled to memory 204A, display 216A (e.g., through a graphics processor or accelerator), and to high-speed expansion ports 210A, which may accept various expansion cards (not shown). In the implementation, low-speed controller 212A is coupled to storage device 206A and low-speed bus 214A. The low-speed bus 214A, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 200A may be implemented in a number of different forms, as shown in the figure. For example, it may be implemented as a standard server 220A, or multiple tunes in a group of such servers. It may also be implemented as part of a rack server system 224A. In addition, it may be implemented in a personal computer 221A or as a laptop computer 222A. Alternatively, components from computing device 200A may be combined with other components in a mobile device (not shown), such as device 250A. Each of such devices may contain one or more of computing device 200A, 250A, and an entire system may be made up of multiple computing devices 200A, 250A communicating with each other.

The computing device 250A may be implemented in a number of different forms, as shown in the figure. For example, it may be implemented as part of electronic visual aid device 99 or any smart/cellular telephone 280A. It may also be implemented as part of a smart phone 282A, personal digital assistant, a computer tablet, or other similar mobile device. Furthermore, it may be implemented as a dedicated electronic visual aid in either a hand held form 290A or a wearable electronic visual aid device 99.

Electronic visual aid device 99 includes a processor 252A, memory 264A, an input/output device such as a display 254A, a communication interface 266A, and a transceiver 268A, along with other components. The device 99 may also be provided with a storage device, such as a Microdrive or other device, to provide additional storage. Each of the components of Electronic visual aid device 99, 252A, 264A, 254A, 266A, and 268A, are interconnected using various buses, and several of the components may be mounted on a common motherboard or in other manners as appropriate.

The processor 252A can execute instructions within the electronic visual aid device 99, including instructions stored in the memory 264A. The processor may be implemented as a chipset of chips that include separate and multiple analog and digital processors. The processor may provide, for example, for coordination of the other components of the device 99, such as control of user interfaces, applications run by device 99, and wireless communication by device 99.

Processor 252A may communicate with a user through control interface 258A and display interface 256A coupled to a display 254A. The display 254A may be, for example, a TFT LCD (Thin-Film-Transistor Liquid Crystal Display) or an OLED (Organic Light Emitting Diode) display, or other appropriate display technology. The display interface 256A may comprise appropriate circuitry for driving the display 254A to present graphical, video and other information to a user. The control interface 258A may receive commands from a user and convert them for submission to the processor 252A. In addition, an external interface 262A may be provided in communication with processor 252A, so as to enable near area communication of device 99 with other devices. External interface 262A may provide for example, for wired communication in some implementations, or for wireless communication in other implementations, and multiple interfaces may also be used.

The memory 264A stores information within the electronic visual aid device 99. The memory 264A can be implemented as one or more of a computer-readable medium or media, a volatile memory unit or units, or a non-volatile memory unit or units. Expansion memory 274A may also be provided and connected to device 99 through expansion interface 272A, which may include, for example, a SIMM (Single In Line Memory Module) card interface. Such expansion memory 274A may provide extra storage space for device 99, or may also store applications or other information for Electronic visual aid device 99. Specifically, expansion memory 274A may include instructions to carry out or supplement the processes described above, and may include secure information also. Thus, for example, expansion memory 274A may be provided as a security module for device 99, and may be programmed with instructions that permit secure use of device 99. In addition, secure applications may be provided via the SIMM cards, along with additional information, such as placing identifying information on the SIMM card in a non-backable manner. The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 264A, expansion memory 274A, or memory on processor 252A, that may be received, for example, over transceiver 268A or external interface 262A.

Electronic visual aid device 99 may communicate wirelessly through communication interface 266A, which may include digital signal processing circuitry where necessary. Communication interface 266A may provide for communications under various modes or protocols, such as GSM voice calls, SMS, EMS, or MMS messaging, CDMA, TDMA, PDC, WCDMA, CDMA2000, GPRS, EDGE, 3G, 4G, 5G, AMPS, FRS, GMRS, citizen band radio, VHF, AM, FM, and wireless USB among others. Such communication may occur, for example, through radio-frequency transceiver 268A. In addition, short-range communication may occur, such as using a Bluetooth, Wi-Fi, or other such transceiver such as wireless LAN, WMAN, broadband fixed access or WiMAX. In addition, GPS (Global Positioning System) receiver module 270A may provide additional navigation- and location-related wireless data to device 99, and is capable of receiving and processing signals from satellites or other transponders to generate location data regarding the location, direction of travel, and speed, which may be used as appropriate by applications running on Electronic visual aid device 99.

Electronic visual aid device 99 may also communicate audibly using audio codec 260A, which may receive spoken information from a user and convert it to usable digital information. Audio codec 260A may likewise generate audible sound for a user, such as through a speaker, e.g., in a handset of device 99. Such sound may include sound from voice telephone calls, may include recorded sound (e.g., voice messages, music files, etc.) and may also include sound generated by applications operating on device 99. Part of the electronic visual aid device is a speaker and microphone 120. The speaker and microphone may be controlled by the processor 252A and are configured to receive, generate and convert audio signals to electrical signals, in the case of the microphone, based on processor control.

An IMU (inertial measurement unit) 280A connects to the bus, or is integrated with other components, generates and provides data regarding the orientation of the electronic visual aid device 99. This IMU can contain a compass, such as a magnetometer, an accelerometer and/or gyro, to provide directional data, impact and shock data or other information or data regarding shocks or forces experienced by the electronic visual aid device.

A flasher and/or flashlight 125 are provided and are processor controllable. The flasher or flashlight may serve as a strobe or traditional flashlight, and may include an LED.

Figure 1F:
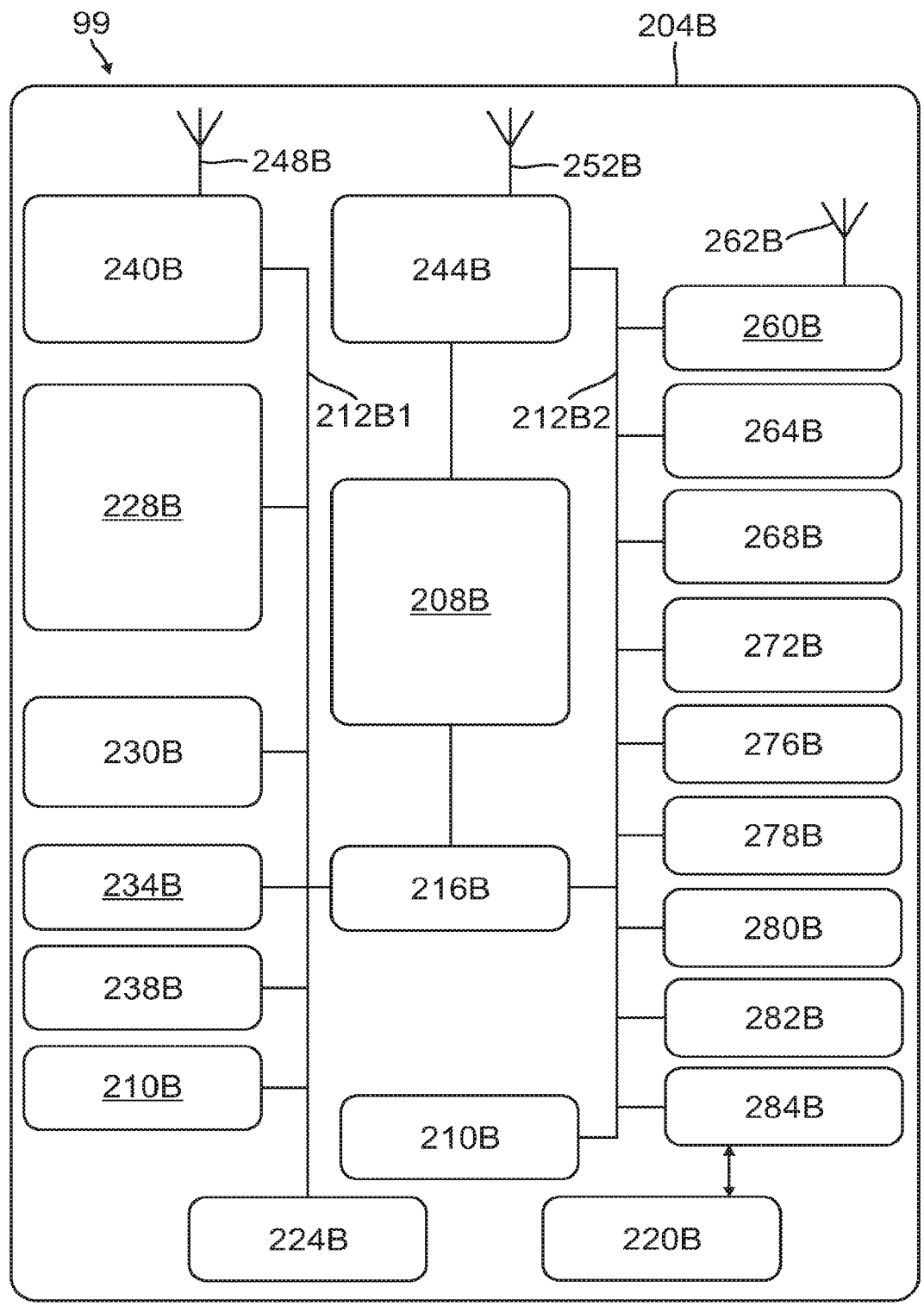
FIG. 1F is one example of an electronic visual aid device, illustrating interrelationship of various elements of the features and detailed components, according to the present disclosure.

Referring now also to FIG. 1F, another schematic is shown which illustrates an example embodiment of electronic visual aid device 99 and/or a mobile device 200B (used interchangeably herein). This is but one possible device configuration, and as such it is contemplated that one of ordinary skill in the art may differently configure the mobile device. Many of the elements shown in FIG. 1F may be considered optional and not required for every embodiment. In addition, the configuration of the device may be any shape or design, may be wearable, or separated into different elements and components. Electronic visual aid device 99 and/or a device 200B may comprise any type of fixed or mobile communication device that can be configured in such a way so as to function as described below. The mobile device may comprise a PDA, cellular telephone, smart phone, tablet PC, wireless electronic pad, or any other computing device.

In this example embodiment, electronic visual aid device 99 and/or mobile device 200B is configured with an outer housing 204B that protects and contains the components described below. Within the housing 204B is a processor 208B and a first and second bus 212B1, 212B2 (collectively 212B). The processor 208B communicates over the buses 212B with the other components of the mobile device 200B. The processor 208B may comprise any type of processor or controller capable of performing as described herein. The processor 208B may comprise a general purpose processor, ASIC, ARM, DSP, controller, or any other type processing device.

The processor 208B and other elements of electronic visual aid device 99 and/or a mobile device 200B receive power from a battery 220B or other power source. An electrical interface 224B provides one or more electrical ports to electrically interface with the mobile device 200B, such as with a second electronic device, computer, a medical device, or a power supply/charging device. The interface 224B may comprise any type of electrical interface or connector format.

One or more memories 210B are part electronic visual aid device 99 and/or mobile device 200B for storage of machine readable code for execution on the processor 208B, and for storage of data, such as image data, audio data, user data, medical data, location data, shock data, or any other type of data. The memory may store the messaging application (app). The memory may comprise RAM, ROM, flash memory, optical memory, or micro-drive memory. The machine-readable code as described herein is non-transitory.

As part of this embodiment, the processor 208B connects to a user interface 216B. The user interface 216B may comprise any system or device configured to accept user input to control the mobile device. The user interface 216B may comprise one or more of the following: keyboard, roller ball, buttons, wheels, pointer key, touch pad, and touch screen. A touch screen controller 230B is also provided which interfaces through the bus 212B and connects to a display 228B.

The display comprises any type of display screen configured to display visual information to the user. The screen may comprise an LED, LCD, thin film transistor screen, OEL, CSTN (color super twisted nematic), TFT (thin film transistor), TFD (thin film diode), OLED (organic light-emitting diode), AMOLED display (active-matrix organic light-emitting diode), retinal display, electronic contact lens, capacitive touch screen, resistive touch screen or any combination of these technologies. The display 228B receives signals from the processor 208B and these signals are translated by the display into text and images as is understood in the art. The display 228B may further comprise a display processor (not shown) or controller that interfaces with the processor 208B. The touch screen controller 230B may comprise a module configured to receive signals from a touch screen which is overlaid on the display 228B. Messages may be entered on the touch screen 230B, or the user interface 216B may include a keyboard or other data entry device.

In some embodiments, the device can include a speaker 234B and microphone 238B. The speaker 234B and microphone 238B may be controlled by the processor 208B and are configured to receive and convert audio signals to electrical signals, in the case of the microphone, based on processor control. This also offers the benefit for additional user interface modes. Likewise, processor 208B may activate the speaker 234B to generate audio signals. These devices operate as is understood in the art and as such are not described in detail herein.

Also connected to one or more of the buses 212B is a first wireless transceiver 240B and a second wireless transceiver 244B, each of which connect to respective antenna 248B, 252B. The first and second transceiver 240B, 244B are configured to receive incoming signals from a remote transmitter and perform analog front end processing on the signals to generate analog baseband signals. The incoming signal may be further processed by conversion to a digital format, such as by an analog to digital converter, for subsequent processing by the processor 208B. Likewise, the first and second transceiver 240B, 244B are configured to receive outgoing signals from the processor 208B, or another component of the mobile device 208B, and up-convert these signals from baseband to RF frequency for transmission over the respective antenna 248B, 252B. Although shown with a first wireless transceiver 240B and a second wireless transceiver 244B, it is contemplated that the mobile device 200B may have only one such system or two or more transceivers. For example, some devices are tri-band or quad-band capable, or have Bluetooth and NFC communication capability.

It is contemplated that electronic visual aid device 99 and/or a mobile device, and hence the first wireless transceiver 240B and a second wireless transceiver 244B may be configured to operate according to any presently existing or future developed wireless standard including, but not limited to, Bluetooth, Wi-Fi such as IEEE 802.11 a,b,g,n, wireless LAN, WMAN, broadband fixed access, WiMAX, any cellular technology including CDMA, GSM, EDGE, 3G, 4G, 5G, TDMA, AMPS, FRS, GMRS, citizen band radio, VHF, AM, FM, and wireless USB.

Also part of electronic visual aid device 99 and/or a mobile device is one or more systems connected to the second bus 212B which also interfaces with the processor 208B. These systems can include a global positioning system (GPS) module 260B with associated antenna 262B. The GPS module 260B is capable of receiving and processing signals from satellites or other transponders to generate location data regarding the location, direction of travel, and speed of the GPS module 260B. GPS is generally understood in the art and hence not described in detail herein.

In some examples, a gyro or accelerometer 264B can be connected to the bus 212B to generate and provide position, movement, velocity, speed, and/or orientation data regarding the orientation of the mobile device 204B. A compass 268B, such as a magnetometer, may be configured to provide directional information to the mobile device 204B. A shock detector 264B, which may include an accelerometer, can be connected to the bus 212B to provide information or data regarding shocks or forces experienced by the mobile device. In one configuration, the shock detector 264B is configured to generate and provide data to the processor 208B when the mobile device experiences a shock or force greater than a predetermined threshold. This may indicate a fall or accident, for example. A pressure sensor 272B can also be utilized for determination of altitude to aid with motion detection.

One or more cameras (still, video, or both) 276B can be provided to capture image data for storage in the memory 210B and/or for possible transmission over a wireless or wired link or for viewing at a later time. For image capture in low lighting situations and additional infrared camera 278B may be included as well, along with a luminance sensor 282B and an additional proximity sensor for location and scene sensing. The processor 208B may process image data to perform the steps described herein. A flasher and/or flashlight 280B are provided and are processor controllable. The flasher or flashlight 280B may serve as a strobe or traditional flashlight, and may include an LED. A power management module 284B interfaces with or monitors the battery 220B to manage power consumption, control battery charging, and provide supply voltages to the various devices which may require different power requirements.

Thus, various implementations of the system and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Unless specifically stated otherwise as apparent from the above discussion, it is appreciated that throughout the description, discussions utilizing terms such as "processing" or "computing" or calculating" or "determining" or "identifying" or "displaying" or "providing" or the like, refer to the action and processes of a computer system, or similar electronic computing device, that manipulates and transforms data represented as physical (electronic) quantities within the computer system memories or registers or other such information storage, transmission or display devices.

Based on the foregoing specification, the above-discussed embodiments of the invention may be implemented using computer programming or engineering techniques including computer software, firmware, hardware or any combination or subset thereof. Any such resulting program, having computer-readable and/or computer-executable instructions, may be embodied or provided within one or more computer-readable media, thereby making a computer program product, i.e., an article of manufacture, according to the discussed embodiments of the invention. The computer readable media may be, for instance, a fixed (hard) drive, diskette, optical disk, magnetic tape, semiconductor memory such as read-only memory (ROM) or flash memory, etc., or any transmitting/receiving medium such as the Internet or other communication network or link. The article of manufacture containing the computer code may be made and/or used by executing the instructions directly from one medium, by copying the code from one medium to another medium, or by transmitting the code over a network.

Figure 2:
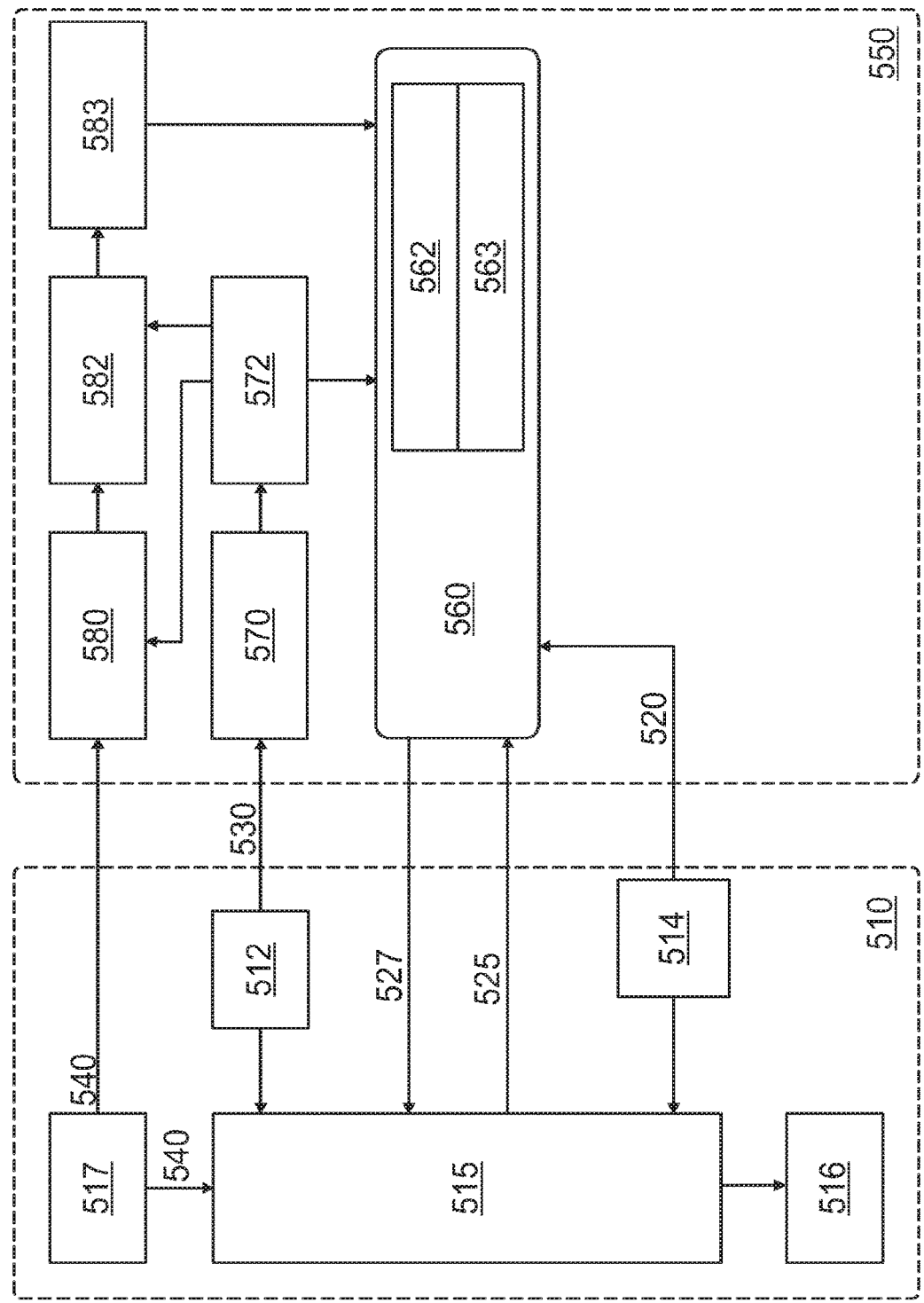
FIG. 2 is a high-level block diagram showing major components, processes, dataflow and interactions for an autonomous control system for low-vision users in an electronic visual aid device.

FIG. 2 is a high-level block diagram showing the main components of the autonomous control system 550 as it interacts with the user and the rest of the electronic visual aid device 510. To preserve clarity, only the principal data and control paths are indicated in the drawing; it should be understood, for example, that an implicit bidirectional connection exists between the coordinator block 560 and all other entities depicted within the boundary of the Autonomous Control System 550. Similarly, the components shown here represent a logical partitioning that does not necessarily constrain the topology of an actual realization; according to common practice, any of these blocks can be further subdivided, rearranged, and recombined in a multitude of ways while still providing the same aggregate functionality.

The block diagram of FIG. 2 may refer to one or more "blocks", "engines", "modules" or the like. As used herein, any "engine", "block", or "module" may include one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

This block diagram is broadly applicable to visual aid devices that are wearable, hand-held (e.g., a smartphone, tablet, or PC), or fixed-mounted. The leftmost portion of the figure, enclosed within a dashed rectangle, depicts one example of a notional device 510 that lacks the autonomous control enabled by the present inventions. In all subsequent text, this shall be known as the Reference 510 since it possesses only standard functionality that will be extended by the systems and methods to be disclosed. Here the reference is represented in greatly simplified form, with nearly all of its functionality abstracted into a monolithic image processing block 515. Regardless of implementation details and feature sets, any reference electronic visual aid can be considered an opaque processor that continuously accepts the raw image stream 540 from the camera(s) 517 as input, applies various computations and manipulations to incoming images as directed by manual user inputs 514 (e.g., buttons, gestures, or voice) with possible mediation by additional sensors 512 (e.g., gyroscopes for image stabilization), and ultimately presents fully-processed images on one or more display devices 516.

The rightmost section of FIG. 2, encapsulated by a second dashed rectangle, comprises an "Autonomous Control System" (ACS) 550 provides the image processing functionality of the electronic visual aid devices described herein. All inputs to the image processing chain (camera images 540, sensor data 530, and user controls 520) must be accessible, along with the current state 527—the collection of settings and parameters that directly control image processing behavior. Various analysis blocks operate on these inputs to construct abstract models of the scene contents and wearer head motion, which are then used to build further models anticipating user intentions, activity, and focus of attention. Relying on trends gleaned from these models, the coordinator 560 is configured to decide what changes, if any, must be made to the device state in order to satisfy the inferred desires of the wearer. Outputs can be transmitted back to the core of the notional device as computed controls that update the current state 527. Although these computed controls are somewhat analogous to user inputs, they are considerably more powerful since the autonomous control system can freely manipulate low-level parameters to adjust the final image with few, if any, restrictions.

For didactic continuity, exposition initially focuses on wearable aspects of the systems described herein, beginning with the simplest configurations and gradually expanding the scope. Once this baseline has been firmly established, it will serve as a reference point that facilitates explanation and understanding of the alternatives.

Wearable Electronic Visual Aids

Wearable visual aids are commonly available on an eyeglass-like or otherwise head-mounted frame, with built-in displays presenting visual information directly toward the eye(s) and forward-looking cameras attached to the frame near the nose, eye, or temple. They can be single self-contained units, or the head-mounted component can be tethered to external battery or computing resources. It is not necessary to co-locate cameras with the frame or to maintain fixed orientation with respect to the head, but observing those conventions greatly simplifies implementation and usability for wearable devices.

Since increased size and weight are undesirable characteristics in wearable devices, there is always a conflict between battery life and hardware capability in fully-portable devices; low-power, low-complexity solutions are needed to provide an equitable balance in this tradeoff. The ACS 550 described here can achieve this goal using a simple wearable reference platform 510 that provides only rudimentary services: a single camera 517 on a fixed mount oriented such that its field of view (FOV) roughly coincides with that of a normally-sighted wearer, gyroscopic sensors 512 producing a continuous real-time stream of angular velocity measurements on at least the yaw and pitch axes of the wearer's head, at least one display device 516, and the ability to intercept and process these data in order to manipulate the state of the visual aid device. Additional cameras and sensors will be shown to enhance the capabilities and attainable performance.

Image Analysis

The image analysis block 580 is responsible for taking camera images corresponding to a single instant in time and locating structures within them that the user would like to examine. In the simplest and most common configurations, a single camera is present so only one image is available. Generally, only a relatively small subset of this input image must be processed; this subset represents the focus-of-attention (FOA) of the user, upon which his or her gaze is actively centered. The FOA will commonly be a fixed area at the image center, since this very often coincides with the natural eye-line of the user as the fixed camera rotates with his or her head. However, it can also fall in a user-specific off-center section for cases involving central visual field deficiencies, with a camera that is eccentrically mounted or otherwise not matching the natural forward line-of-sight of the wearer. In some applications, it may also be a region selected (by the coordinator 560 or scene analysis 582) based on user behavioral trends or the contents of previous and current images, or based on eye-tracking that directly captures gaze direction. In cases where regions of interest are effectively being selected autonomously, the entire input image can also be searched to locate and grade all possible such regions, or selected regions can be omitted. For a camera with a wide enough FOV (larger than a normal human FOV, as with a wide-angle or fisheye lens) or one that is oriented away from the natural sight line of the user, the FOA can even incorporate locales that the user would not physically be able to perceive. Because image analysis is typically a computationally intensive activity, however, it is preferred to limit the size of the sub-image being examined when possible.

Once an FOA has been identified in the input image(s), its content is examined by the ACS 550 to discover features that are deemed to be interesting. Regardless of the specific analysis methods employed, this search can be facilitated by preprocessing the source data using image analysis 580 to increase detection reliability in the presence of poor or non-uniform lighting, electronic noise, and other confounding factors. FOA regions from individual images can be filtered to reduce noise or remove other unwanted interference patterns, increase image sharpness or detail, or increase contrast. A low-power, low-complexity method that yields benefits in most circumstances is to apply standard image processing techniques for increasing global image contrast. More gains can be obtained by with an adaptive contrast enhancement based on the specific FOA image content; given sufficient processing power, sophisticated adaptive algorithms available within the image processing community can be applied to increase local contrast. Data-dependent preprocessing can also be constrained to track and maintain consistency with the statistics of the image as it changes over time. Note that all preprocessing is performed for the benefit of the detection algorithm, and is separate from any operations applied to the image data that will be displayed directly to the user.

When multiple cameras are available, images providing multiple coverage of the FOA can be combined to improve image quality using well-known algebraic transformations (to compensate differences in imaging geometry) and signal processing techniques (to combine pixels that are not coherently or commensurately sampled). Similar well-documented data fusion techniques merges data from image sensors with disparate modalities (e.g., combining a standard visible-light camera and a near-infra-red or thermal imager), or the more exotic modality can simply aid in FOA selection. Alternately, some images or modalities (but not all) can be rejected and omitted based on relative quality or environmental conditions when it is clear that their contribution will not be beneficial.

A broad range of techniques are available within the image processing and computer vision communities for detecting objects of interest in an image. In one example, the features of interest sought by image analysis are text—letters, numerals, and pictograms organized into words, lines, columns, or paragraphs—and shapes that share a text-like structure, e.g., discrete rows of similar-sized glyphs, such as icons on a computer screen. Methods for isolating these structures include the Stroke Width Transform (SWT, which locates lines with consistent width that are likely to be associated with text), optical character recognition (OCR, potentially simplified since only recognition and measurement is needed, not interpretation), and other forms of computer vision including those based on Machine Learning. While all of these are viable for use in this application, they are also computationally intensive and/or tend to be limited to narrowly-drawn domains (specifically text, faces, or a fixed menu of object types) in which they excel. Multiple feature detectors types, all operating in parallel, can be employed and combined at the cost of increased system complexity, for example facial detection algorithms along with text recognition.

Instead, the image analysis of the ACS 550 leverages the power of a low-level technique for extracting Maximally Stable Extremal Regions (MSERs) from input images or image sections. MSER is a standard instrument, found in any comprehensive image processing or computer vision toolbox, sporting low computational complexity and excellent scaling properties as image size increases. Given a carefully-selected set of values for its controlling meta-parameters and an efficient software implementation, MSER reliably isolates the above-described text-like structures when presented with the luminosity component of an image, which can be computed/extracted from the input image itself, particularly when coupled with the contrast-enhancement pre-processing described above. Since MSER is a primitive feature detector, it does not actually recognize letters or text and distinguish them from icons or shapes—the extraction is based entirely on connectivity, color, and local contrast. This simplicity is an advantage, allowing it to run quickly while performing equally well with symbols in any font or language, including cursive handwriting, as well as other regular structures that do not necessarily represent written communication.

Scene Analysis

The output of image analysis 580 is a list of the raw features found in the FOA image, where each feature is literally a list of connected pixels that are visually similar but somehow separable from their surroundings as determined by the meta-parameters driving MSER feature detection. The task of scene analysis 582 is to transform this unorganized list into a coherent data structure that grants insight into the structure and content of the image so that spurious features can be distinguished from text and other meaningful structures. A vast body of public literature spanning many decades of research effort is devoted to methods of discovering such patterns from similar data structures—these Statistical Pattern Recognition, Pattern Classification, Neural Network, and Machine Learning techniques have proven very effective but come at a high cost in preparation (e.g., data-gathering), processing complexity, or both. In this disclosure, a much simpler and more intuitive hierarchical analysis process works just as well.

The first step in this process is removal of spurious features, outliers, and ambiguous detections by the scene analysis 582 block. Individual detected shapes are examined and discarded if they are lie outside carefully tuned bounds for length, width, pixel count, or aspect ratio. Some of these suppressions can be performed automatically by MSER, but scene analysis permits more complicated criteria. For example, one useful heuristic is to reject all shapes that intersect the top or bottom edge of the FOA (since their true vertical extent has not been plumbed), but not to reject shapes just because they touch the right or left side as long as they are sufficiently wide but avoid intersecting both sides. Additionally, features having a vertical center (halfway between their upper and lower vertical limits) too far from the vertical center of the FOA are also rejected. The precise selection of thresholds and bounds for acceptance and rejection is the key to biasing the autonomous system toward responding to features that are more or less "text-like;" deliberate adjustments can be made, for example, such that the device reliably ignores anything that does not unambiguously comprise printed text.

Following the initial cull, remaining features are divided into groups containing items that appear to be in the same row. This is not done by explicitly assigning a row to each feature (an ill-defined procedure), but rather implicitly, in multiple steps, beginning with the construction of a model for the probability density function (pdf) of the vertical centers for the shapes via a traditional kernel-density estimation procedure. When multiple detected objects are organized into coherent rows—even a single row that contains a few character-like shapes, and even when slight rotational deviation from horizontal alignment is present—distinct pdf peaks arise at the vertical position of each row, with the width and height of the peak giving insight into the statistical quality of the "horizontal rows of objects" hypothesis. For detecting vertically-oriented text such as found in Eastern cultures, columns can be considered instead of rows.

Once again, a complex heuristic or Machine-Learning model can be used to decide if the detected set of shapes truly possesses the row-like, column-like, or paragraph-like structure. In practice, however, a lower-complexity technique proves sufficient. Scene analysis 582 selects the highest peak detected and retains only those features affiliated with that peak. It further prunes features for which the estimated pdf value is too small, typically less than 90% of the peak value. A final cull eliminates any fully-enclosed shapes (i.e. shapes-within-shapes, to remove internal topological "holes" found by MSER), followed by any remaining features with a vertical height that is significantly different from the average height (to eliminate outliers). There is considerable art to be exercised in selecting the optimum rejection thresholds, because the standard deviation can easily exceed the mean when there are few enough remaining samples; however, the actions taken in refining the focus model (below) serves to ameliorate the negative impact of a suboptimal setting.

As a result of these filtering operations, the statistics of the remaining shapes differ from those of the originally detected peak in the pdf. However, the pool of candidate features is now self-consistent in terms of height and position. Note that scenes with large deviations from horizontal alignment with the camera sensor plane are automatically pruned in the above-described process due to the smearing of the pdf that occurs as vertical centers are spread by the rotation.

Scene Model

The final output of scene analysis 582 is primarily two numbers: the estimated height of the objects remaining in the pool (which of course determines the amount of zoom required, if any) and some measure of the statistical confidence that these objects indeed represent a row of text or text-like structures and are not the result of a statistical fluke and random noise. This pair of values comprises the scene model 583, a statistical snapshot based on a single image. (The final set of features that contributed to these two numbers can also be considered part of the model, but only for display purposes and not further analysis or decisions.)

Ultimately, results from single scene analysis 582 attempts are not sufficiently robust to obtain repeatable performance across a wide range of conditions—hence the introduction of the focus model, 563, which will be described in detail below. However, a solid and intuitively sensible starting point assigns a quality score proportional to the total width of any remaining objects that survived the pruning process. An alternate metric is the total height of all pdf peaks for due only to the final surviving features (but this metric must be carefully normalized before it can be compared across frames). For the more complex version of scene analysis, where higher-order structures such as parallel rows or columns (or paragraphs) are directly considered, an analogous pair of statistics can be derived by deeper analysis of the structure and consistency of the pdf (i.e., the relationships between peak locations, their heights, and their widths).

Motion Analysis

The Motion Analysis block 570 takes inputs from various sensors that measure motion of the electronic visual aid device 510 and constructs a motion model 572. At a minimum, the sensor data stream must include angular velocity on the yaw and pitch axes of the user's head so that sudden and/or gross changes in orientation can be quickly detected. Accelerometer measurements are also a valuable indicator of significant translational motion, but are optional.

When available, an eye-tracking sensor that reports eye motion will obviously be of great value in determining the user's true FOA. This data can be forwarded to the coordinator 560 and image analysis blocks 580 for this purpose, but can also be used in building the motion model 572 as described below.

Motion Model

At a minimum, the motion model 572 is simply an indicator of the steadiness of the camera and wearer's head in the wearable case. This can of course be determined by noting changes in head orientation, but contemporary commodity sensor hardware only yields accurate orientation measurements when augmented by additional hardware (beyond gyroscope measurements) and relatively expensive processing (e.g., an extended—hence nonlinear—Kalman filter). Fortunately, angular velocity readings produced by ubiquitous solid-state gyroscopes are sufficient for this purpose despite their endemic poor long-term drift characteristics.

When a sufficiently high angular velocity manifests, it invariably accompanies a sharp head motion indicative of a sudden change of FOA. These high angular velocity movements, or sudden changes of FOA by the user of the visual aid device, can be used by the motion model to determine or indicate that the user of the visual aid device is engaged in animated movement, and is therefore not engaged in deliberate concentration or attempting to focus their attention on something within the field of view. Typically, the autonomous system does not want to perform costly computations or to make visually distracting changes to processing or image enhancements (particularly field-of-view) while the user is engaged in animated movement. Conversely, very small angular velocity values maintained over a perceptible interval can reasonably be interpreted by the motion model as deliberate concentration by the user, or an attempt by the user to engage in focused attention on something within the field of view. Intermediate angular velocity values can be associated with reading, scanning, or searching behavior. While angular velocities associated with these behaviors are lower than those associated with an animated movement state, they can be higher than the angular velocities associated with a focused attention state in which the user of the visual aid device is very still. Regardless, these intermediate angular velocity values, such as those associated with reading, scanning, or searching behavior, can still be interpreted by the motion model as indicating that the user is in a focused attention state in which the user is deliberately concentrating on something within the field of view. In contrast to the animated movement state, the autonomous system typically does want to apply processing and/or image enhancements when the user is engaged in a focused attention state, such as automatically zooming or applying contrast enhancements to text like structures, faces, or other objects of interest within the field of view. As shown below (FIG. 2 and accompanying text), this three-state motion model 572 is capable of realizing practical autonomous control despite its simplicity.

When accelerometer data is available, the motion model can be further refined by reliably distinguishing between a stationary or moving user. This is a valuable distinction because it is undesirable to make dramatic unbidden changes to the visual characteristics of an individual who is in motion, especially when moving quickly or negotiating stairs and other obstacles. Accelerometers also enable discrimination between uniform motion and accelerated (irregular) motion—thus, the device might permit vision changes for a passenger riding in a vehicle even if rapid translation is detected.

Eye tracking information 530, when available, is not directly a part of the motion model but is included because it serves the same purpose as the motion model: contributing to the activity model, which is a high-level description of what the user is currently doing. Just as large angular velocity or acceleration measurements can indicate that the user has not yet settled his or her FOA, eye movements also tell when the device can save power and avoid performing image analysis.

Activity Model

Whereas the motion model 572 is a snapshot of short-term movement (typically over an interval no longer than a few video frames or approximately 50-250 milliseconds, the activity model 562 represents an attempt to follow the user's motions over a longer term in order to glean intentions and anticipate future movements.

In the simplest case, a degenerate activity model 562 includes the instantaneous motion model 572; this is still powerful enough to yield complex behavior (exemplified in FIG. 3 and its accompanying description) and a satisfactory user experience. However, the expenditure of more computational resources enables considerably more sophistication to be realized. For example, applying machine learning, such as a Hidden Markov Model (HMM) that distinguishes multiple states associated with situations in which the user of the visual aid device is engaged in deliberate concentration, or a focused attention state. For example, reading motions such as scanning or movement from side to side (of the head and/or eye) allows the activity model 562 to recognize that a user is steadily reading from left to right, backtracking, searching downward and leftward for the next line, moving to the next facing page, or transitioning to a non-reading behavior. HMMs achieve high reliability by continually updating a statistical model for each possible state that takes into account the history of observations and the likelihood of the tentatively-detected state transitions. Tracking transitions into and out of tasks and subtasks this way allows the ACS 550 to react differently when the user is reading text vs inspecting other non-textual structures; for example, small changes in zoom level due to noise in font size measurement can be completely suppressed since text organized into paragraphs does not typically change in size except in quantum leaps.

Additional common activities or behaviors can be recognized and tracked using HMMs. Furthermore, a generic HMM can be updated and adapted—either off-line or continuously, in real-time—with new measurements to capture or ignore idiosyncratic user characteristics; an example is accommodating instability (Parkinson's disease or other involuntary movements) or recognizing a limited range of motion. Manual use feedback, such as immediate incremental changes requested immediately after an autonomous change, can also drive adaptation of HMMs.

Focus Model

The scene model 583 described above is a two-parameter statistical model that is based on a single image frame. The focus model 563 is a more reliable representation of the contents of the FOA that is incrementally maintained even as the scene model 583 changes instantaneously. In its simplest form, it still comprises only two parameters: an estimated size and a statistical confidence level. However, these values are updated on consecutive image frames, incorporating trends revealed by the time-series of scene model values.

When the scene model 583 changes dramatically (in its size estimate), the focus model 563 is reset and subsequently has a low statistical significance. If the scene model size estimate remains consistent, even with relatively low confidence, the focus model continually accumulates confidence. Slight variations in size estimates are accommodated by a filter that weights recent scene models more heavily than older estimates while updating the model prior to accepting it.

Coordinator

The coordinator 560 ties all of the other blocks in the ACS 550 together, coordinating their activities and managing their resources. Combining the information provided by the various analysis and model blocks, the coordinator 560 is configured to decide when sufficient statistical confidence exists in its model of the user's activity and focus for it to initiate a change in the state of the device. In doing so, it carefully gauges both the desirability and safety of any action before scheduling or executing the alteration. The coordinator also keeps track of user-initiated device controls, because certain deliberate user inputs might override and potentially delay autonomous decisions. In particular, manual controls are provided to restore the Default View (defined below) or trigger Image Analysis and automatic view adjustment. Tracking these inputs is also important because incremental manual changes requested immediately after an autonomously-directed change provides corrective feedback indicating some degree of user dissatisfaction with the autonomous decision; these inputs can be used to train and update the autonomous response characteristics. When multiple analysis types operate simultaneously, the coordinator provides arbitration among multiple processes (and the user) each requesting changes, to ensure that overall device state remains consistent. Arbitration between user inputs and autonomous processes considers and rejects (or accepts) groups of related changes rather than individual adjustments in isolation.

Figure 3:
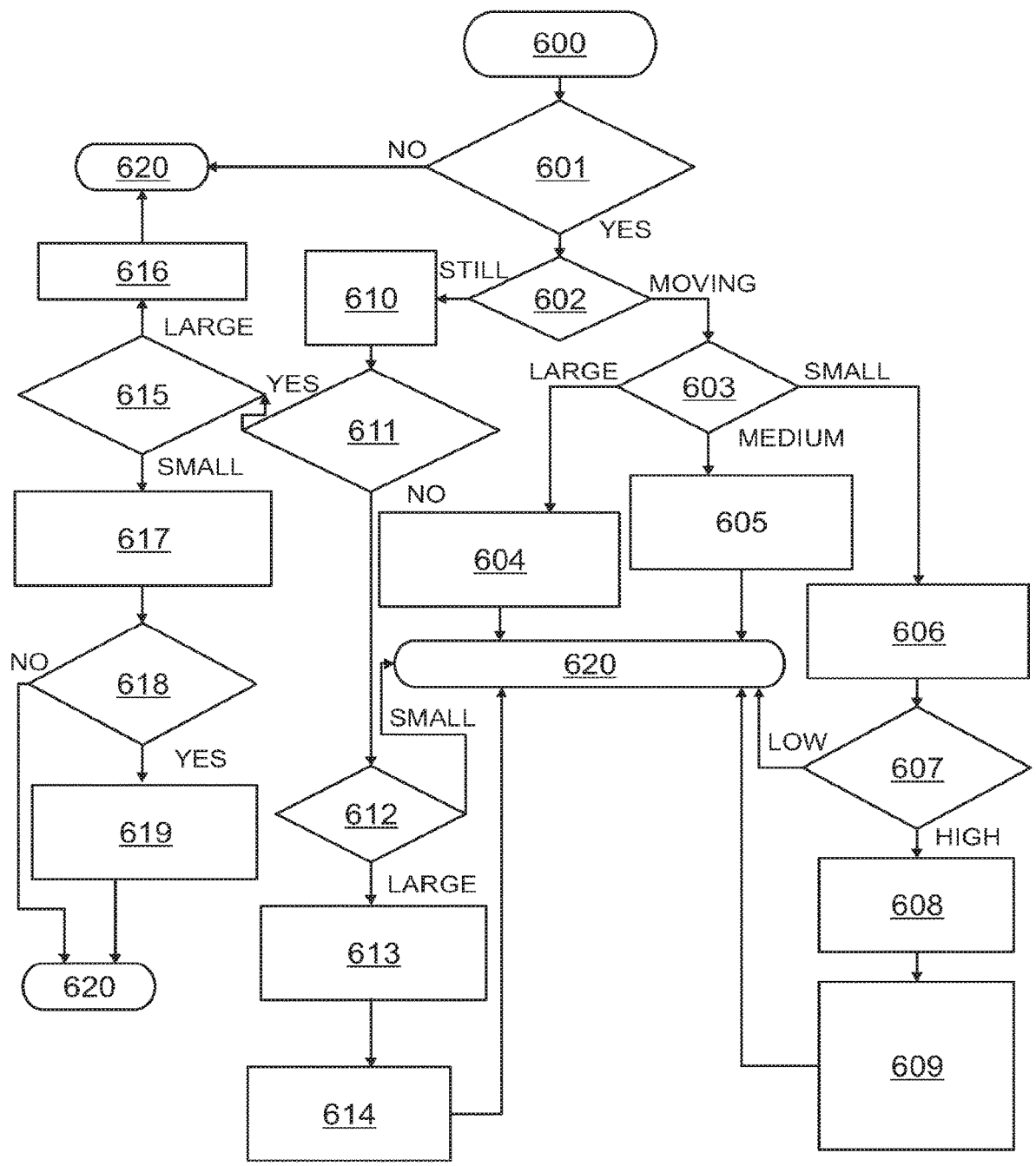
FIG. 3 is a high-level flowchart depicting one possible realization, particularly well-suited to low-power applications, of the Coordinator block that performs autonomous control of the magnification and field-of-view in a wearable electronic visual aid device.

FIG. 3 is a high-level flowchart for one preferred realization of the coordinator 560 that is particularly well-suited to low-power applications. This flowchart constitutes a predictive model for the behavior of the human operating the device that implements its algorithm, allowing the device to anticipate the wearer's needs and respond accordingly. To achieve this, it requires only low-precision gyroscope sensor measurements of head-induced camera rotation, and does not rely on absolute position/angle estimates, long-term gyroscope stability, or advanced data fusion algorithms. Note that the flowchart and accompanying explication (below) consistently use qualitative or non-specific labels such as "LARGE," "SMALL," "HIGH", "LOW", and "Threshold" to represent numerical quantities; precise values of these parameters must be selected in accordance with application-specific performance tradeoffs goals, but their detailed specification is unnecessary for the understanding of the algorithm.

The algorithm(s) presented herein is lightweight enough to run on every frame. Hence, processing according to the flowchart can begin with START block 600 every time a new video frame becomes available. DELAY TIMER STATUS Block 601 then determines whether to continue processing or to terminate computations immediately (at DONE block 620). Its decision is based on the state of a delay timer maintained by the state machine inherent in the flowchart structure. This timer is set deliberately in order to pace events and reduce power consumption, since all computations are suspended while the delay timer counts downward toward expiration. When the delay timer has expired or is otherwise inactive, computation continues with CURRENT STATE block 602.

CURRENT STATE Block 602 selects between two paths based on the current operating state. The two possible states are MOVING or STILL. Generally speaking, MOVING obtains at startup or when significant motion has been detected in the electronic visual aid device 510 and remains in effect until the electronic visual aid device 510 remains sufficiently stationary at the same time that an automatic view update determination is made with high confidence. The STILL state is only entered once such a high-confidence automatic view change decision has been made, and persists even in the presence of smooth motions (such as the regular scanning associated with reading) until a sufficiently large or sharp movement of the electronic visual aid device 510 is encountered. CURRENT STATE block 602 branches to RECENT MOTION block 603 when MOVING, or to INCREASE MOTION COUNT block 610 when STILL.

Blocks 603-609 are all associated with the MOVING state. RECENT MOTION Block 603 considers trends in angular velocity over the recent past, using the Motion Model to look backward no more than a few frames and branching one of three ways based on the detected movement pattern.

For a large angular velocity, a sudden change in head orientation and concomitant re-orientation of attention is inferred— RESET ZOOM block 604 handles this by resetting the view characteristics to a nominal setting (typically a wide angle with minimal processing and little or no magnification) to afford the largest field-of-view that a user can use to seek a new focus-of-attention. The delay timer is also set to a large value, typically 1-2 seconds, because it will take at least this long for the user to re-orient. Note that it is possible for all of this to occur while the view characteristics are already set to this nominal position; this condition is transparent to the operation of the algorithm and causes no problems, with the action of block 604 simply not producing a visible change.

On the other hand, very small angular velocities from the motion model can indicate that the user is attempting to maintain a steady focus or focused attention, perhaps in an attempt to read text or discern small features. ANALYZE VIDEO Block 606 is configured to confirm this hypothesis by analyzing the input video frame, applying preprocessing and using image & scene analysis operations from FIG. 2. This process performs a full characterization of the size, shape, and distribution of the detected objects or regions upon which the user is apparently focusing, producing a scene model that estimates the optimal amount of magnification needed for comfortable viewing. Trends in the scene model can be captured by a focus model that bides idly until it develops high statistical confidence that the user is intently focusing on a subject that maintains a consistent appearance over time. DETECTION CONFIDENCE Block 607 terminates computation if the detection confidence level is not yet sufficient. If confidence does breach the necessary threshold, APPLY ZOOM block 608 applies the inferred zoom level by adjusting the magnification and triggers any other related view changes; it also caches the current rotation state (which does not need to be known relative to any absolute coordinate system) as the current Reference Orientation. RESET ALL STATISTICS Block 609 prepares for the imminent change in magnification by resetting all statistics and changing the state to STILL; it also sets the delay timer to a large value, typically 2-4 seconds during which computations can be elided since another sudden change in magnification is generally undesirable.

RESET DETECTION STATISTICS Block 605 handles the remaining possibility—that recent angular velocities have been neither very large nor very small. In this case, all detection statistics are reset and the delay timer is set to a moderate value (typically approximately one-half second) so that a brief refractory delay is enforced before further analysis can occur even if the user immediately holds very still.

Blocks 610-619 are associated with the STILL state. Note that, with the exception of the transition from MOVING to STILL triggered by block 609, the delay timer is never active during STILL in order to avoid missed detections of transient motions. Instead, a motion count is maintained to tally consecutive STILL frames and limit the frequency of expensive computations. INCREASE MOTION COUNT Block 610 increments this motion count. Then, MOTION COUNT THRESHOLD Block 611 compares the latest motion count to a threshold (typically corresponding to 0.25 to 0.75 seconds of time).

If the motion count is not large enough, no video analysis will occur. Instead, recent rotational motion trends over the recent past (typically not more than a few frames) from the activity model are examined in RECENT MOTION block 612. If those motions are sufficiently small, processing ends with DONE block 620. Otherwise, a large or fast head motion has been detected and a re-orientation of attention is inferred; RESET ZOOM block 613 then resets the view to its nominal value (exactly as in block 604), sets the delay timer to a relatively long delay (typically 1-2 seconds, again as in block 604), and changes the operational state to MOVING block 614.

On the other hand, if motion count exceeds its threshold, CHANGE FROM REF ORIENTATION block 615 is entered. This block compares the current device orientation (i.e. the rotational state, accumulated from all gyroscope measurements since the last time a reference orientation was set) with the reference orientation. If the difference in orientation is large enough (typically 10-12 degrees in yaw or 5-8 degrees in pitch) then STATE=MOVING block 616 is entered, changing the operational state to MOVING since the wearer's focus of attention has drifted significantly (albeit smoothly and slowly) from the last reference orientation. Otherwise, ANALYZE VIDEO block 617 resets the motion count and performs image & scene analysis of the latest video frame, updating all internal models in an attempt to determine the user's focus of attention and an appropriate accompanying view setting. If no change is yet justified, the algorithm terminates in DONE block 620. Otherwise, UPDATE ZOOM block 619 updates the view setting and resets the Reference Orientation to the current orientation.

An important consideration that does not exist for analogous MOVING-state blocks 606-608 is ingrained in the GO/NO-GO decision made by CHANGE ZOOM block 618 in order to obtain more consistent and aesthetically pleasing behavior in blocks 617-619. Estimates of the size of features being observed invariably contain a moderate amount of random noise or systematic error that subsequently propagates to the computed estimate of the optimal magnification level. When the predicted amount is sufficiently close (but not identical) to the current setting, changing the zoom setting too eagerly or often leads to as visually unpleasant "breathing" phenomenon as the algorithm responds to statistical errors rather than actual feature size changes; this happens frequently when measuring small objects (e.g., less than 15-20 pixels in height, where a single pixel represents a significant percentage error). Heuristics must be employed to separate actual trends from spurious measurements without incurring noticeable latency penalties. This is achieved by requiring higher statistical confidence for accepting small changes, and by enforcing different confidence thresholds for increments vs. decrements (e.g., accept small increases more readily than small decreases).

Wearable Pragmatics

Thus far, the discussion has focused on how the ACS can infer user FOA and sufficient intent to decide when it is appropriate to initiate changes. Little has been said about the specific nature of these changes other than mentioning the need to compute the amount of magnification needed. This is because, in a wearable visual aid, magnification is the dominant parameter of interest. Since the camera moves in lockstep with the head, without eye-tracking it is natural to restrict the FOA to a small central or other fixed location in the image; even with eye-tracking, the inferred and analyzed FOA can be small.

The amount of magnification needed is easily determined by maintaining a user-dependent setting for a preferred size—typically the size at which reading becomes comfortable. When the detected feature size is smaller than this preference, magnification must be applied. Typically, when it is larger than the preference, there is no need to reduce the displayed size. However, for some users large text is also problematic, and there is an optimum size that must be enforced. If the objects in the FOA can be further discriminated, a different preferred size can be assigned to text vs.

other content. If the user is consistently noticed to further adjust magnification after an autonomous change, the stored preference can automatically be updated, potentially only conditionally for the specific original source size (since image quality can also depend on that original size). FIGS. 4A, 4B, and 4C demonstrate the operation of autonomous magnification with a preferred target size in an electronic visual aid device. An additional simplifying assumption, for didactic purposes, is that the focus-of-attention is always directed toward the center of the camera image.

FIG. 4A is example of an unprocessed camera image of a scene containing only text, taken directly from its source camera and shown to the user on a display. This figure exemplifies the displayed view of the scene prior to the application of any manual or automatic adjustment of the electronic visual aid. The text illustrated here has portions with differing font sizes. In particular, the line of text 801 has a certain font height, while line of text 802 has a different and slightly larger height. For purposes of discussion, is assumed that that all of the text in FIG. 4A, on both lines 801 and 802, is too small for the user to read, and hence requires magnification.

For illustrative purposes, also assume that the autonomous control system has previously been configured with a preferred target size that is 50% larger than text on the display labelled as 802, and 114% larger than what is labelled 801. Then, when the autonomous control system for magnification is engaged and the captured camera image appears as shown in FIG. 4A, the autonomous system will automatically increase magnification so that the display appears as in FIG. 4B. Here, the output line of text 804 is a magnified version of the input line of text 802, while line 803 is a correspondingly magnified version of line 801 from the source image. Line 804 now has a height that matches the preferred target size (i.e., total applied magnification is by a factor of 1.5× for a 50% increase in size). Note that if the user were to move the camera a short distance directly away from the text being viewed, the autonomous system would respond by further increasing the magnification, maintaining the appearance of FIG. 4B as it works to keep line 804 at the preferred target size.

Referring back to FIG. 4A, when the user pans the camera upward so that line 801 becomes the focus of attention, the autonomous system will respond with additional magnification, resulting in a display that resembles FIG. 4C. Here, the output line of text 805 is a magnified version of line 801, while line 806 is a magnified version of line 802 from the source image; now, total applied magnification is by a factor of ×2.14 for a 114% increase in size. Line 805 has the same height on the display in FIG. 4C as line 804 does in FIG. 4B, because the detected structures (e.g., text in this example) in the focus-of-attention are adjusted to the meet the preferred target size. Because line 802 in the unmodified image is larger than line 801, its magnified image in line 806 actually exceeds the target size.

If the user repeatedly pans the camera to alternate between viewing lines 801 and 802 in the focus-of-attention, the autonomous control system can be configured to respond by adjusting magnification such that displays resembling FIGS. 4B and 4C, respectively, result.

In the introductory summary to this document, it was noted that the ACS can control not only the degree of magnification, but also the size and nature of the FOV. PCT Pat. App. No. PCT/US2019/034443, filed May 29, 2019, described how the view can be divided into a central region (circular, oval, or rectangular) with uniform magnification, a transition zone with the amount of zoom tapering gradually down to a fixed level (most often unity, or no magnification) at its edge, and a periphery maintaining this final fixed magnification; this partitioned configuration delivers increased detail for easier viewing at the center without compromising overall FOV to maintain context and situational awareness.

The situation herein is considerably more flexible: the parameters of this partitioning (i.e., sizes of the inner and outer shapes bounding the transition zone with tapered magnification) can be linked to the amount of magnification such that they vary over a continuum rather than remaining static or having a few discrete settings. This extra degree of freedom allows for natural and intuitive views: with high amounts of zoom, more area is required to show a magnified subject and the contents of the periphery diminish in importance. If the objects within the FOA can be further discriminated, the view can be customized to the specific task by applying different continuously-varying profiles e.g., for reading text vs. faces or other image content.

Alternately, the size of the magnified region can be adjusted to fully encompass the dominant detected features—at least up to a certain specified size limit. Of course, falling back to a regime of pure magnification (with no partitions) also remains a viable as the ultimate low-power option.

Also mentioned above is the existence of a "nominal view." This user-specific configuration may or may not have any processing associated with it; according to preference, it could result in an unmodified copy of the camera image or apply an optional partition profile with magnification. For example, video images presented to the user in a nominal view or with nominal settings may be presented without substantial enhancements or adjustments applied to the real-time images. For purposes of this discussion, "substantial enhancements" can be interpreted as noticeable enhancements to the real-time images such as adjusted magnification, adjusted contrast, magnification of structures of interest, contrast enhancements to subjects of interest, magnification of identified faces, etc. Non-substantial enhancements can be considered to be minor or common image processing improvements such as color correction, brightness correction, noise reduction, etc.

An important pragmatic aspect of the disclosure in its wearable aspect relates to timing. Delays must be carefully tuned so that device responds rapidly to changes in feature size or motion, but not so quickly that spurious changes produce distracting or confusing visual effects. Most importantly, settings that have visible aspects should not be changed instantaneously because rapidly implemented visual effects may leave the user disoriented. Instead, changes to magnification, partition radii, or other geometric parameters can be animated to complete gradually over a period of several seconds; the sense of homotopy inherent in this slow distortion process allows the user to register what is happening, fully appreciate and anticipate the end result of the visual changes, and potentially cancel it. Active animation timescales are also chosen to mesh well with the refractory periods described for the flow chart and state diagram of FIG. 3.

Finally, there is the displayed image, which is of course subject to both the normal processing provided by the non-autonomous subset of the electronic visual aid and the viewpoints (magnification and FOV) chosen by the ACS. It can be advantageous to display (when requested or otherwise under user control) visual indicators highlighting either the detected features or some simple structures that summarize them (such as a bounding box). This extends to more than just the final dominant features that contributed to the latest scene model—visually highlighting other features in the FOA (particularly when the FOA is very large or encompasses the entire display) for a brief interval, or persistently (with periodic updates as scene content changes) can guide the user's eye (and subsequently the center of the FOA) to other areas of interest.

Assisted Reading

For wearable electronic visual aids, it has been assumed above that the camera acts as a proxy for the eye, whether or not there is some visual deficiency present. Thus, the ACS does not actively select or steer the FOA because the wearer has a natural inclination (in the absence of eye-tracking) to point the ersatz eye toward an intended target.

A slight modification remains compatible with this usage model but provides an additional level of assistance when reading. If, as described above, a Hidden Markov Model is used to recognize the activity of reading and further distinguish the associated left-to-right and right-to-left scanning phases, then rotational motion sensors can be used to provide a combination of smoothing and amplification to these head-scanning motions.

Decoupled Camera

All previous treatment of wearable electronic visual aids has subscribed to a focus-follows-head paradigm. However, there is another viable usage model that remains intuitively easy to use. In this alternate mode, the image source is a handheld camera that is not rigidly fixed with respect to the user's eyes; instead, the user can directly manipulate the FOA by pointing the camera to capture images of directions or locales that cannot comfortably be seen simply by moving the head. The remote image source can be a dedicated camera or device specifically intended for use with the visual aid, a webcam that happens to be attached to a nearby accessible computer, or a generic mobile phone or tablet executing an application that provides remote streaming video via a wireless network connection (or alternately, the remote device can delegate full or partial control back to the wearable electronic visual aid).

This modality somewhat resembles "first person viewing" applications for remote-controlled aircraft, with an important difference: the camera is always firmly attached to the user, whose innate kinesthetic and proprioceptive senses maintain orientation with respect to the world. Also, the user can always switch back to the standard head-driven regime while remaining confident that the resulting viewpoint shift will never be too dramatic or disorienting (since it is both user-requested and hence expected). See also the section below on Handheld Devices for further aspects of the remote camera.

Meanwhile, the user can leverage the entire gamut of processing and analysis capabilities provided by the electronic visual aid, including image enhancement and automatic magnification of detected features. Alternately, those features can also be accomplished directly on the processor and GPU of the remote camera. Additionally, the user now gains the benefit of additional lighting, image sensor, and lens options. A very common use case involves close inspection of fine details, which would normally be performed using a magnifying glass placed within inches of the target: head-mounted cameras do not function well in such circumstances—focusing at close distances is difficult without a macro lens, and head-shadowing result in poor lighting on the subject. Nearly every mobile phone, however, provides close-focus macro capabilities and a light source.

Note that while using a remote camera source, motion sensor measurements of head movements must be ignored for the purpose of inferring specific activity (e.g., via HMMs) but can still indicate whether the user is receptive to an autonomous change.

Hand-Held Electronic Visual Aids

A hand-held electronic visual aid is a portable device containing essentially the same hardware and software as a wearable device—hence it shares the attributes shown in FIG. 2 and FIG. 3 and capabilities previous discussed—but does not have displays or cameras mounted in a fixed position with respect to the head or eyes of the user (e.g., the displays and/or cameras of a smartphone or tablet are seldom in a fixed position relative to the head or gaze of the user). Thus its usage model would seem to closely resemble the decoupled camera mode described above as an optional for wearables. However, the change in form factor introduces new degrees of freedom and nuances to be exploited.

The typical form factor is a mobile telephone, computing tablet, or tablet-like device with a flat display surface that is hand-held or extemporaneously propped-up using a stand. For the purposes of this discussion, such a device mounted on an articulated arm is included in the "hand-held" category since it is intended to be aimed positioned by hand despite its otherwise fixed mounting point. A camera (typically just one, though more can be accommodated as described above) faces the opposite direction from the display surface. With no fixed relationship with respect to the head or eyes of the user, there is no longer a natural inclination to treat the device as an ersatz eye linked to head motion; in fact, there is every expectation that its FOA can be directed independently, as in Decoupled Camera mode. Instead, the relative locations of display and camera hint that the device should be treated like a handheld magnifier, by pointing the rear of the display toward the subject and looking directly into the display. Though that is an apt metaphor, this configuration is in fact even more flexible than an autonomous magnifying lens.

With wearables, there is pressure to constrain the displayed FOV to match the normal extent of the human eye to avoid disorienting the user during extended continuous usage. For hand-held devices, this is no longer a consideration—the user benefits from a device that affords the widest possible field of view, from which the user or device can select an FOA. The wide field of view is provided by a wide-angle or fisheye lens. For commercial tablets not specifically designed to be visual aids, the camera may not have a particularly wide viewing angle (though many are significantly wider than the human FOV); in these cases, inexpensive lenses are readily available that can be attached by magnets or clamps, with compensation for the lens distortion characteristics either preprogrammed or adaptively calculated (a standard procedure found in all computer vision toolboxes). Similar attachments use mirrors to redirect the effective look direction of the camera with respect to the display should the default configuration prove to be awkward or uncomfortable.

With this wider field of view and a display that is physically much larger than those of a wearable device, along with reduced need for low weight, it becomes economical to perform the extra computations needed to apply Image Analysis to a larger area, potentially the entire display. Complete models (scene, activity, and focus models) only need to be maintained for a single chosen FOA that by definition dominates the user's attention, but the results of image analysis (or a reduced version thereof) can highlight or draw attention to multiple potential areas of interest (text or otherwise) elsewhere on the screen. Here the portal-like effect of the partitioned regions with tapered magnification combines synergistically with the larger display: the user now has the ability to view the magnified area comfortably while still being provided with more context than was possible with a wearable device. The extent of the FOA can now also be measured, and the size of the magnified region expanded to encompass more—or all—of it while still maintaining context. The ACS still acts autonomously within the FOA, but that FOA is no longer constrained to be central. Changing the FOA becomes a manual user-initiated task, but all other ACS tasks continue without intervention—along with a new activity: autofocusing the camera each time the FOA changes.

Without the direct connection linking the user gaze direction to the camera, the Motion Model becomes less important for capturing detailed user intent (e.g., tracking sub-states while reading), but is still used to detect gross movement and avoid performing computations or making changes at inappropriate times.

Because the device is intended to be manipulated by the hands, the use of buttons and touch-screen sequences to operate it is natural and unobtrusive; such controls are used to choose a new FOA, adjust the size of the partitions (e.g., the width of the magnified area or the taper profile), or make other adjustments. Intuitive touch-based interfaces are already in wide use for performing similar or analogous manipulations related to controlling cameras or examining captured photographs on tablets or mobile phones.

Even though it will normally be possible to orient the camera toward a new FOA that was formerly located in the periphery of the display, the fixed relationship between the camera and display will often require the user to tilt the device in order to view it comfortably. This invariably results in perspective distortion that would not be apparent for a subject that is viewed squarely by the eye or camera. An optional feature enables the Image Analysis task to detect the geometric trends associated with off-axis viewing and apply a compensatory adjustment. A similar capability is found in phone-based document scanners, but that technology operates on large-scale exterior shapes (e.g., a sheet of paper) which yield robust statistics rather than finer-scale features like words and lines of text. Furthermore, document scanners treat that exterior shape and its rectified contents as their final product, whereas the visual aid device merges the locally-rectified content into a larger gestalt that is not necessarily transformed.

Geometric reprojection can also be used to simulate a different camera tilt in order to make simultaneous pointing and viewing with the tablet more comfortable; here a fixed non-central FOA associated with the camera image is shown centrally on the display and transformed to compensate for the difference in geometry between the simulated and actual camera angle.

Finally, another feature to include on a visual aid device built on a phone or tablet platform is the ability to record snapshots taken from the camera image for later "playback" and examination on the same device. This is distinguishable from simply viewing captured digital photos or even from the "freeze and examine" modes found on virtual reality glasses or other wearable visual aids because the full range of analytical controls including ACS capabilities can be applied to the image—the difference is that motion inputs must be ignored since the input is no longer live video.

Mounted Electronic Visual Aids

Here, "mounted" does not necessarily mean completely immobile, merely that the display is not generally intended to be moved during the ordinary course of use. A typical form factor would resemble a computer monitor with a touchscreen, where the display surface can be adjusted to face the user for comfortable viewing, but there is no expectation that it will be carried around or pointed toward a subject or scene. In this form factor, computing power, display size, and resolution are inexpensive resources. Similarly, battery capacity and power consumption are unimportant factors.

Some major changes and new opportunities result from stationary operation. First, motion sensors are no longer necessary or useful. Instead, only the touchscreen-based control interface drives the selection of FOA. The camera does not need to be mounted at the rear of the display—it can be entirely separate, fully portable or on a relocatable mount. In classroom settings or other situations where multiple users can share a camera or choose among multiple cameras, image sources can be mounted on a wall or in a remote location. Now the use of a high-resolution camera, calibrated wide-angle or fisheye lens, and full-frame perspective correction to simulate different camera location are of paramount importance. Touchscreen controls for choosing FOA allow the user to pan virtually over a wide area, potentially assembled from multiple cameras with partially-overlapping views (as a way to maintain high resolution instead of trading it for wider per-sensor FOV). With the addition of these capabilities, a group of users at different locations within a room can share a small number of cameras and simulate the operation of a portable handheld electronic visual aid using only their fixed-mounted displays.

Amidst these changes, the same ACS algorithms and operations (other than motion detection and modeling) described above remain applicable to draw attention to potential FOAs containing text or other interesting content, and to provide automatic setting of magnification and other view characteristics for the chosen primary FOA.

Enhanced Detection

MSER-based feature detection delivers excellent performance at a very low resource cost. When suitable resources are available, it is straightforward to utilize the framework described above by using the raw MSER outputs as input to more sophisticated scene-analysis techniques or to apply additional analysis schemes directly to the source images. The results of parallel analyses can be combined by the Coordinator and fused with more complex motion cues before making a decision. In this way, the visual aid can automatically react in qualitatively different ways to fundamentally different situations (e.g., text vs. human faces). More importantly, the introduction of Machine Learning based recognition brings with the possibility of adapting to user preferences and idiosyncrasies based on interactive user feedback.

Autonomous Contrast Control

Previous sections of this document have described a general framework for autonomous control, but have focused primarily on the specific application to autonomous manipulation of magnification and field-of-view. Presented here is a corresponding autonomous system for enhancing contrast built on the same framework. It can operate stand-alone, or synergistically with the previously described autonomous system for magnification.

There are many ways to apply real-time contrast enhancement to an image. Among the well-established techniques are simple contrast scaling (which linearly adjusts the luminance of each image pixel proportionally farther away from neutral gray), linear and nonlinear contrast stretching (including arbitrary gamma profile adjustment) that applies a monotonic function to luminance, unsharp masking and similar forms of edge enhancement. All of these methods have relatively low-complexity efficient GPU-based implementations that operate upon a single target pixel at a time or restrict their computations to using a small neighborhood of pixels surrounding the target pixel. Each has one or more degrees of freedom controlled by parameters that vary the amount or other characteristic(s) of the contrast enhancement. Allowing the parameters of a contrast enhancement method to change over time, or to vary spatially within a single image, does not greatly impact implementation complexity. However, analyzing an image to determine the optimum amount of contrast enhancement to apply to each target pixel or even globally to the whole image is computationally expensive because it generally requires the collection of image statistics such as histograms via a process that is inherently serial in nature and hence not well suited to modern parallel GPU architectures.

However, when the systems described above for effecting autonomous control of magnification are available, the additional task of automatically choosing an appropriate level of contrast enhancement for interactive users is simplified because intermediate analysis products leading to the go/no-go decision to zoom as well as the determination of the amount of magnification needed are available for use in further analyses. These intermediate computations provide considerable information about the contents of the FOA and the structure of the objects that the wearer is examining. As described above, this includes not only the locations or bounding-boxes of individual pictograms or words, but also incorporates further processing that groups tentative words or adjacent shapes into distinct rows, rejects noisy or inconsistent data, and assesses the reliability of its decisions over time and as the contents of the viewed scene change.

When text or text-like structures are detected within the FOA, whether magnification will also be adjusted or not, it is reasonable to assume that the user is intent upon examining these structures and desires that contrast improvement be applied preferentially to those structures. Factors to be considered in determining the type and/or magnitude of contrast enhancement or adjustment include the type of image to be enhanced (e.g., fine patterns with sharply-delineated luminosity transitions such as text or line drawings, which are well-suited to edge enhancement vs. more gradually-varying natural patterns that are better enhanced via true local-contrast adjustment), size of features to be enhanced (potentially measured by the autonomous magnification system), amount of magnification applied (whether autonomously or manually), the existing contrast between dominant foreground and background luminosities, whether there is a dark foreground against a light background or vice versa, and whether the background is simple (e.g., a single solid color) or complex (e.g., when text overlays a pattern or natural image). The amount and type of motion (e.g., head motion) present may also be a desired factor.

Computational complexity is greatly reduced by quantifying these factors only over the extent of well-qualified and reliably-identified structures within the FOA. The achievable reduction in complexity is illustrated in the series of FIGS. 5A, 5B, 5C, and 5D.

Figures 5A, 5B, 5C, 5D:
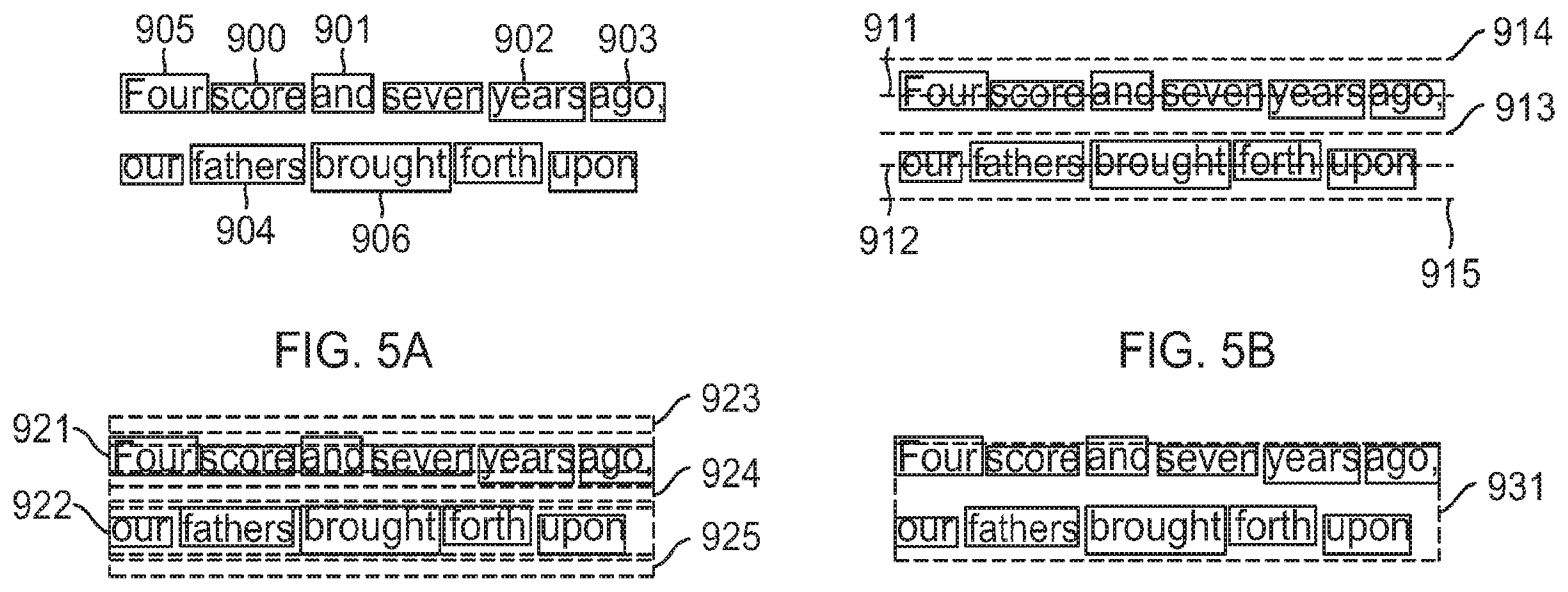

FIG. 5A depicts a possible result of analysis of an image of some dark text against a light background for the purpose of autonomous control of magnification. Rectangles (900-906) denote regions that were determined to be text or text-like in nature. In this example, the rectangles call out individual words but in practice closely spaced words are often merged and individual letters are sometimes individually detected or omitted—these details do not materially alter the nature or results of this discussion; the crucial point is that image analysis has already identified likely features of interest to the viewer, discarding noise and outliers while retaining shapes with consistent sizes found in row-like formations. Note that these rectangles are not uniform in height; rectangle 900 has minimum height, while rectangles 901 and 904 are taller due to ascenders in the text. Similarly, rectangles 902 and 903 are both taller and shifted downward because they contain descenders and/or punctuation extending below the font baseline. Shape 905 contains a capital letter that extends its height, and the rectangle for word 806 combines the effects of both ascenders and descenders.

FIG. 5B shows how all the information necessary to optimize contrast settings for the detected objects can be obtained while examining only a minimal number of pixels in the image when informed by the results of shape detection. Dashed lines 911 and 912 each pass through every rectangle contained in their respective rows. Analyzing only the pixels that fall along such a line provides enough statistical information about the distribution of image luminosity among background and text to support a contrast stretch or other contrast adjustment that will enhance viewing of the detected text. A single detected row (e.g., the most central, or the one with largest horizontal extent), or the combined statistics for any subset of all detected rows, can be used for this purpose. Foreground and background can be distinguished (to determine light-on-dark vs. dark-on-light) by examining pixels on lines such as 913, 914, or 915, which are located near detected shapes but do not contain any detected shapes.

Use of only pixels along a small number of lines, as shown in FIG. 5B, will be reliable when the detected shapes truly do comprise text against a plain background. Examining more pixels, as demonstrated in FIGS. 5C and 5D, will give improved results with only a modest increase in computational cost. For example, the presence and nature of a complex background (such as would occur when text overlays an image from the outdoor world) can be detected by analyzing the spectral content and/or wavelet decomposition of small rectangular areas such as 923, 924, and/or 925 that are reasonably assumed to contain only "background" due to their proximity to detected content. Similar analysis of rectangular areas such as 921 (which only includes vertical regions are common to all shapes in that row), 922 (which incorporates the union of all vertical regions occupied by any shape in the row), or 931 (which encompasses the union of limits of all detected shapes) have been demonstrated to distinguish reliably between text and non-text content (such as multicolor icons or buttons). Spectral or wavelet analysis of pixels along a one-dimensional foreground line (such as 911 or 912) can also be used to distinguish text from non-text, but is not likely to yield consistent results over a wide range of scene conditions.

The analysis of a limited area allows rapid computation of contrast settings or adjustments that are optimal or near-optimal for that limited area, and presumably suitable for nearby areas if not the entire image. Those settings can be applied globally (to the entire displayed image), can be limited to some region containing the analyzed area and some or all of the FOA, or can manifest a tapered profile such that optimal computed settings are applied to some or all of the FOA while gradually trending toward a designated default or neutral setting in peripheral regions. There is no significant additional computational load associated with this spatially-dynamic profile because the contrast setting is computed based only on location and is not dependent on the contents or statistics of the pixels affected.

An autonomous contrast control system that leverages the analysis products of an accompanying autonomous magnification system fits within the same FIG. 2 framework previously described here for autonomous magnification. When both are present, nearly all of their functionality will be shared. The exception is the Coordinator block, 560, which will be augmented or replaced (depending on whether or not autonomous contrast is present in the system) as described below.

On the other hand, if autonomous magnification is not present at all (or is disabled), then it is still possible to realize an efficient, low-complexity autonomous control system that has the same block diagram as FIG. 2. Without the advanced analysis provided by autonomous magnification, new implementations for image analysis (580), scene analysis (582), and scene model (583) must be provided. One simple implementation only examines pixels in a designated FOA. As described above, this FOA can be fixed, customized to the user, context-dependent (e.g., adjusted based on motion, magnification, and/or recent activity), or even relocated in real-time (e.g., with eye-tracking). Consideration of existing magnification is particularly useful in reducing complexity, since a visible image shown magnified by factor M in a displayed FOA actually contains $M^2$-fold fewer pixels to analyze. The simplified autonomous contrast control system would only attempt (e.g., via spectral or wavelet analysis) to determine whether the FOA contains significant high-frequency content with well-defined edges (such as text or line drawings) or smoothly-varying imagery; this is the extent of the scene modeling effort. If text is indicated, then further analysis of FOA histogram statistics will allow fine-tuning of computed contrast settings and detection of light-on-dark vs. dark-on-light rendering.

Figure 6:
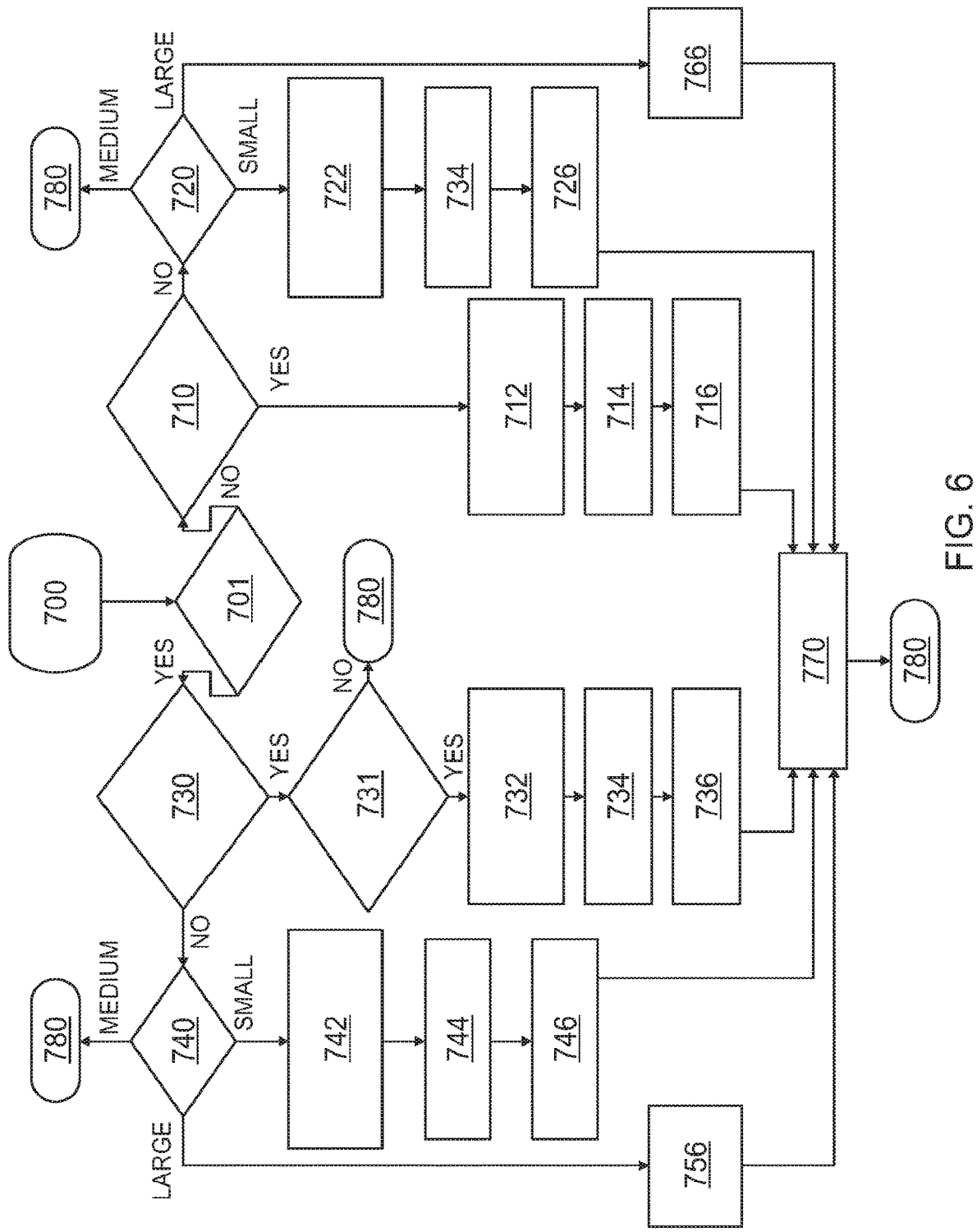
FIG. 6 is a high-level flowchart depicting one possible realization, particularly well-suited to low-power applications, of the Coordinator block that performs autonomous control of contrast in the wearable electronic visual aid device.

Thus, regardless of whether or not autonomous magnification is present, the framework described above and in FIG. 2 can be applied for autonomous contrast adjustment and the remaining discussion subsumes both cases transparently. FIG. 6 shows one example of a flowchart depicting the high-level operation of a low-complexity coordinator (560) for autonomous contrast control that works whether or not autonomous magnification is available, and also when autonomous magnification is available but disabled. If both autonomous systems are present, this flowchart represents a coordinator process that operates in parallel with the process represented by the flowchart in FIG. 3.

As in FIG. 3, the flow of FIG. 6 begins with block 700 at the start of each new video frame. Block 701 makes a decision between two processing paths depending on whether or not the current level of magnification is greater than unity. When there is magnification, the left branch to block 730 is taken; otherwise, there is currently no magnification (i.e., unit magnification prevails) and the right branch to block 710 is taken.

For this right branch, corresponding to no magnification, block 710 checks to see whether the autonomous magnification system has requested a change in magnification for the current video frame. If there is no autonomous magnification capability in the system, or it is present but disabled, or has not made such a request then operation continues with block 720. Otherwise, block 712 examines the results of the intermediate products produced by the autonomous magnification system and uses the pre-qualified structures (detected shapes and rows or columns) to determine the relevant set of pixels in the FOA of the image to be analyzed for contrast adjustment. Block 714 then performs the analysis of these pixels (e.g. using statistical, spectral, and/or wavelet techniques), and block 716 computes the new contrast settings that are determined to be optimal for viewing. These settings are then passed to block 770, which applies the most recent contrast setting as described below.

Note that block 712 is distinct from analogous blocks 722, 732, and 742 on alternate processing paths because the specific process for determining relevant pixels can differ depending on the context and circumstances that led to choosing any given path. Similarly, analogous blocks 714, 724, 734, and 744 are separate because the type of analysis performed depends on whether pre-qualified analysis products (e.g., from autonomous magnification) are available, whether any magnification is active, and other contextual clues. Finally, analogs 716, 726, 736, and 746 are also distinct because the available choices for contrast enhancement types and the method of computing their parameters may also be context-dependent.

Block 720 continues processing when there is currently no magnification and there is no request from an autonomous magnification system to increase the magnification. In this case, a decision is made based on recent measured motion (as determined by motion sensors on the device, by image analysis, or other side-information). When large or sudden motions are present, the user is assumed not to be intently focusing on the displayed image, so the autonomous contrast system is effectively reset by choosing designated neutral or default contrast settings in block 766. If motion is very small, the user is assumed to be concentrating on viewing the display; then block 722 determines the relevant pixels in the FOA (without benefit of autonomous magnification analysis products), block 724 analyzes those pixels (e.g., using statistical, spectral, and/or wavelet techniques), and block 726 uses the results of that analysis as well as knowledge of the current contrast settings to compute appropriate updated contrast settings. For both large and moderate motions, computed settings are passed to block 770, which applies the most recent contrast setting as described below. A third case exists for block 720: moderate recent motions that do not definitively connote either fixed attention or deliberate movements are assumed to be associated with reading or scanning behavior, and do not result in any change to the contrast settings; processing then ends at block 780 until the next video frame arrives. Note that the classification of recent motion as "large," "small," or "moderate" (medium) can be arbitrarily complex since they can take into account the output of the Motion Model block (572 in FIG. 2).

For the left branch leaving block 701, corresponding to the presence of magnification, block 730 checks whether autonomous magnification is enabled. When it is disabled or not present, processing will continue with block 740. If it is enabled, block 731 checks whether the autonomous magnification system has updated its analysis products on the current frame. If not, processing ends at block 780 until the next video frame arrives. When new information is available, block 732 uses the associated shapes and data structures to determine the relevant subset of pixels from the source image to analyze, preferably employing a combination of the efficient techniques exemplified in FIGS. 5A-5D. Block 734 then analyzes this set of pixels (e.g. using statistical, spectral, and/or wavelet techniques), and block 736 computes the new contrast settings that are determined to be optimal for viewing. These settings are then passed to block 770, which applies the most recent contrast setting as described below.

When block 730 finds that autonomous magnification is not present or disabled, block 740 makes a decision based on recent measured motion (as determined by motion sensors on the device, by image analysis, or by other side-information). When large or sudden motions are present, the user is assumed not to be intently focusing on the displayed image, so the autonomous contrast system is effectively reset by choosing designated neutral or default contrast settings in block 756. If motion is very small, the user is assumed to be concentrating on viewing the display; then block 742 determines the relevant pixels in the FOA (without benefit of autonomous magnification analysis products), block 744 analyzes those pixels (e.g. using statistical, spectral, and/or wavelet techniques), and block 746 uses the results of that analysis as well as knowledge of the current contrast settings to compute appropriate updated contrast settings. For both large and moderate motions, computed settings are passed to block 770, which applies the most recent contrast setting as described below. A third case exists for block 730: moderate recent motions that do not definitively connote either fixed attention or deliberate movements are assumed to be associated with reading or scanning behavior, and do not result in any change to the contrast settings; processing then ends at block 780 until the next video frame arrives. Note that the classification of recent motion as "large," "small," or "moderate" (medium) can be arbitrarily complex, taking into account the output of the Motion Model block (572 in FIG. 2); it does not necessarily mirror the motion criteria used by block 720.

Block 770 serves as a common rendezvous point for all six paths in FIG. 6. It keeps track of the most recent request for autonomous contrast setting, and makes changes to the device state that actuates these changes. Depending on the magnitude and type of change, this block may schedule an animation that gradually causes the new settings to come into effect; the animation will either complete on its own (independent of the flowchart in FIG. 6) or will be overridden/rescheduled upon the next engagement of block 770. For example, changes caused by deliberate, large-scale motions or that accompany a significant change in magnification (which is a visually disruptive event) can be made abruptly without disorienting the user. On the other hand, transitions in contrast during reading and scanning should be more gradual; in any case, visible "flickering" of settings must be avoided, and block 770 is responsible for filtering the progression of requested vs. actuated settings to provide a more comfortable user experience. When this block determines that autonomous control requests are inconsistent or unreliable, e.g., varying wildly or rapidly over an extended time scale, it can override the request or bias the device toward a neutral setting. Once block 770 is finished with its activities, processing ends at block 780 until the next video frame arrives.

While preferred embodiments of the present disclosure have been shown and described herein, for those skilled in the art such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others.

Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. In addition, the logic flows depicted in the figures do not require the particular order shown, or sequential order, to achieve desirable results.

Furthermore, other steps may be provided or steps may be eliminated from the described flows, and other components may be added to, or removed from, the described systems. Accordingly, other embodiments are within the scope of the following claims.

What is claimed is:

1. A method of providing enhanced vision for a low-vision user, comprising the steps of:
   receiving real-time video images with a visual aid device;
   identifying, with the visual aid device, a subset of each of the real-time video images corresponding to a focus of attention of the low-vision user;
   extracting, with the visual aid device, structures of interest within the subset of each of the real-time video images;
   examining the extracted structures of interest with the visual aid device; and
   discarding structures of interest that include parameters that are outside of pre-selected bounds identifying, with the visual aid device, at least one group of structures of interest that are organized in a row or column;
   determining, with the visual aid device, a dimension of the at least one group of structures of interest;
   adjusting, with the visual aid device, a magnification of the at least one group of structures of interest to match a preferred structure dimension;
   forming, with the visual aid device, an enhanced video stream that includes the real-time images and the at least one group of structures of interest with adjusted magnification; and
   displaying the enhanced video stream on a display of the visual aid device.

2. The method of claim 1, wherein the subset comprises a fixed area of pixels within each of the real-time video images.

3. The method of claim 2, wherein the fixed area of pixels is at a central portion of each of the real-time video images.

4. The method of claim 1, wherein the structures of interest comprise text-like structures.

5. The method of claim 1, wherein the structures of interest comprise facial structures.

6. The method of claim 1, wherein the structures of interest are selected from the group consisting of letters, numerals, pictograms, glyphs and icons.

7. The method of claim 1, wherein the visual aid device automatically identifies the subset of each of the real-time video images based on behavioral trends of a user of the visual aid device.

8. The method of claim 7, wherein behavioral trends of the user comprise a user history of input control sequences and a timing of these input control sequences.

9. The method of claim 1, wherein the visual aid device automatically identifies the subset of each of the real-time video images based on the contents of previously processed video images.

10. The method of claim 1, further comprising:
tracking a gaze of the low-vision user with the visual aid device; and
wherein the visual aid device automatically identifies the subset of each of the real-time video images based on the gaze of the low-vision user.

11. The method of claim 1, further comprising preprocessing the subset of real-time video images to reduce noise or accommodate other unwanted interference patterns.

12. The method of claim 11, where in the preprocessing comprises enhancing a contrast component of the subset of real-time video images.

13. The method of claim 11, wherein the preprocessing comprises increasing a sharpness component of the subset of real-time video images.

14. The method of claim 11, wherein the preprocessing comprises increasing a detail component of the subset of real-time video images.

15. The method of claim 1, wherein the extracting step further comprises extracting maximally stable extremal regions from the subset of real-time video images.

16. The method of claim 1, wherein the pre-selected bounds include a length threshold parameter.

17. The method of claim 1, wherein the pre-selected bounds include a width threshold parameter.

18. The method of claim 1, wherein the pre-selected bounds include a pixel-count threshold parameter.

19. The method of claim 1, wherein the pre-selected bounds include an aspect ratio threshold parameter.

20. The method of claim 1, wherein identifying the at least one group of structures of interest that are organized in a row or column further comprises:
modeling a probability density function of vertical centers for the structures of interest, wherein the probability density function includes one or more pdf peaks;
identifying a maximum peak from the pdf peaks of the probability density functions; and
retaining only structures of interest that are statistically likely to be associated with the maximum peak.

21. The method of claim 20, wherein structures of interest that are statistically likely to be associated with the maximum peak comprises structures of interest that are consistent in size.

22. The method of claim 1, further comprising determining, with the visual aid device, a statistical confidence that the at least one group of structures of interest are organized in a row or column.

23. The method of claim 22, wherein adjusting a magnification of at least one group of structures of interest further comprises adjusting a magnification of the at least one group of structures of interest to match the preferred structure size when the statistical confidence is above a confidence threshold.

24. The method of claim 1, wherein the receiving step further comprises:
obtaining real-time video images with a camera of the visual aid device; and
receiving the real-time video images from the camera with a visual aid device.

25. The method of claim 24, further comprising:
sensing a motion component of the visual aid device as it obtains the real-time video images;
determining a motion state of the visual aid device based on the sensed motion component; and
wherein the adjusting a magnification step, the forming an enhanced video stream step, and the displaying the enhanced video stream step are performed only if the motion state comprises a focused attention state.

26. A method of providing enhanced vision for a low-vision user, comprising the steps of:
receiving real-time video images with a visual aid device;
identifying, with the visual aid device, a subset of each of the real-time video images corresponding to a focus of attention of the low-vision user;
extracting, with the visual aid device, structures of interest within the subset of each of the real-time video images;
determining, with the visual aid device, a dimension of the at least one group of structures of interest;
determining, with the visual aid device, a statistical confidence that the at least one group of structures of interest are organized in a row or column;
adjusting, with the visual aid device, a magnification of the at least one group of structures of interest to match a preferred structure dimension, wherein adjusting a magnification of at least one group of structures of interest further comprises adjusting a magnification of the at least one group of structures of interest to match the preferred structure size when the statistical confidence is above a confidence threshold;
forming, with the visual aid device, an enhanced video stream that includes the real-time images and the at least one group of structures of interest with adjusted magnification; and
displaying the enhanced video stream on a display of the visual aid device.

27. A method of providing enhanced vision for a low-vision user, comprising the steps of:
obtaining real-time video images with a camera of a visual aid device;
sensing a motion component of the visual aid device as it obtains the real-time video images;
determining a motion state of the visual aid device based on the sensed motion component;
receiving the real-time video images from the camera with a visual aid device;
identifying, with the visual aid device, a subset of each of the real-time video images corresponding to a focus of attention of the low-vision user;
extracting, with the visual aid device, structures of interest within the subset of each of the real-time video images;
determining, with the visual aid device, a dimension of the at least one group of structures of interest;
adjusting, with the visual aid device, a magnification of the at least one group of structures of interest to match a preferred structure dimension only if the motion state comprises a focused attention state;
forming, with the visual aid device, an enhanced video stream that includes the real-time images and the at least one group of structures of interest with adjusted magnification; and
displaying the enhanced video stream on a display of the visual aid device only if the motion state comprises a focused attention state.

* * * * *